US011986328B2

(12) United States Patent
Thornton et al.

(10) Patent No.: US 11,986,328 B2
(45) Date of Patent: May 21, 2024

(54) COMPRESSION PADDLES FOR BREAST BIOPSIES

(71) Applicant: MEMORIAL SLOAN KETTERING CANCER CENTER, New York, NY (US)

(72) Inventors: Cynthia M. Thornton, New York, NY (US); Ernesto R. Hermosura, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 22 days.

(21) Appl. No.: 17/051,425

(22) PCT Filed: Apr. 30, 2019

(86) PCT No.: PCT/US2019/030051
§ 371 (c)(1),
(2) Date: Oct. 28, 2020

(87) PCT Pub. No.: WO2019/213165
PCT Pub. Date: Nov. 7, 2019

(65) Prior Publication Data
US 2021/0219926 A1 Jul. 22, 2021

Related U.S. Application Data

(60) Provisional application No. 62/664,682, filed on Apr. 30, 2018.

(51) Int. Cl.
A61B 6/04 (2006.01)
A61B 10/02 (2006.01)

(52) U.S. Cl.
CPC .......... A61B 6/0435 (2013.01); A61B 6/0414 (2013.01); A61B 10/02 (2013.01)

(58) Field of Classification Search
CPC ............... A61B 10/02; A61B 17/3403; A61B 2017/3407; A61B 2017/3411;
(Continued)

(56) References Cited

U.S. PATENT DOCUMENTS 5,595,177 A * 1/1997 Mena ..................... A61B 6/502
378/68
5,678,549 A * 10/1997 Heywang-Koebrunner ................
G01R 33/285
600/417

(Continued)

FOREIGN PATENT DOCUMENTS

WO WO-2010/078048 A2 7/2010
WO WO-2010102087 A1 * 9/2010 ........... A61B 6/0414

OTHER PUBLICATIONS

International Search Report and Written Opinion on PCT/US2019/030051 dated Jul. 12, 2019 (10 pages).

Primary Examiner — Dani Fox
Assistant Examiner — Soorena Kefayati
(74) Attorney, Agent, or Firm — Foley & Lardner LLP

(57) ABSTRACT

Described herein are paddles for breast biopsies. A reverse paddle and a compression paddle may be used in a breast biopsy. Both paddles may each have an aperture. When pressed against the breast, the reverse paddle and the compression paddle may allow the breast to bulge out of the aperture of both paddles during the biopsy. As the breast tissue bulges out of both paddles, the breast tissue to be examined via biopsy may be enlarged, thereby lessening the use of excisional biopsies on subjects with thin breasts.

14 Claims, 25 Drawing Sheets

(58) Field of Classification Search
CPC ..... A61B 5/708; A61B 6/0414; A61B 6/0435; A61B 90/17; A61B 6/502; A61B 6/4417; A61B 10/0041; A61B 10/0233; A61B 6/4035
See application file for complete search history.

(56) References Cited

U.S. PATENT DOCUMENTS

| | | | | |
|---|---|---|---|---|
| 5,803,913 | A * | 9/1998 | Khalkhali | A61B 6/0435 600/407 |
| 5,855,554 | A * | 1/1999 | Schneider | A61B 6/0414 600/407 |
| 6,102,866 | A * | 8/2000 | Nields | A61B 90/17 600/407 |
| 6,304,770 | B1 * | 10/2001 | Lee | A61B 6/502 600/427 |
| 2004/0092826 | A1 * | 5/2004 | Corbeil | A61B 6/0435 600/476 |
| 2005/0228267 | A1 * | 10/2005 | Bulkes | G01R 33/307 600/415 |
| 2008/0043905 | A1 * | 2/2008 | Hassanpourgol | A61B 6/0435 606/130 |
| 2008/0071164 | A1 * | 3/2008 | Pogue | A61B 5/055 600/411 |
| 2008/0084961 | A1 * | 4/2008 | Keppel | A61B 6/0414 382/128 |
| 2008/0146905 | A1 * | 6/2008 | Keppel | A61B 6/037 600/407 |
| 2009/0143674 | A1 * | 6/2009 | Nields | A61B 90/17 600/437 |
| 2009/0171244 | A1 * | 7/2009 | Ning | A61B 6/0435 378/37 |
| 2009/0175408 | A1 * | 7/2009 | Goodsitt | A61B 6/502 378/208 |
| 2009/0292244 | A1 * | 11/2009 | Flagle | A61B 17/3403 604/116 |
| 2010/0067648 | A1 * | 3/2010 | Kojima | A61B 6/502 378/11 |
| 2010/0249648 | A1 * | 9/2010 | Nakata | A61B 90/11 378/37 |
| 2011/0092983 | A1 * | 4/2011 | Pawar | A61B 90/17 600/562 |
| 2012/0130234 | A1 * | 5/2012 | O'Connor | A61B 10/0233 250/393 |
| 2012/0150034 | A1 * | 6/2012 | DeFreitas | A61B 6/502 250/363.04 |
| 2013/0137964 | A1 * | 5/2013 | Schellenberg | G01R 33/481 600/411 |
| 2013/0165765 | A1 * | 6/2013 | Nishihara | A61B 8/0825 600/407 |
| 2013/0303895 | A1 * | 11/2013 | Littrup | A61B 34/20 600/424 |
| 2014/0150182 | A1 * | 6/2014 | Nishihara | A61G 13/122 5/601 |
| 2015/0168509 | A1 * | 6/2015 | Yang | A61B 90/17 600/567 |
| 2016/0022364 | A1 * | 1/2016 | Defreitas | A61N 5/1039 600/429 |
| 2016/0296186 | A1 * | 10/2016 | Hugg | A61B 6/502 |
| 2016/0310215 | A1 * | 10/2016 | Palma | A61B 34/10 |
| 2017/0231575 | A1 * | 8/2017 | DeFreitas | A61G 13/122 128/845 |

* cited by examiner

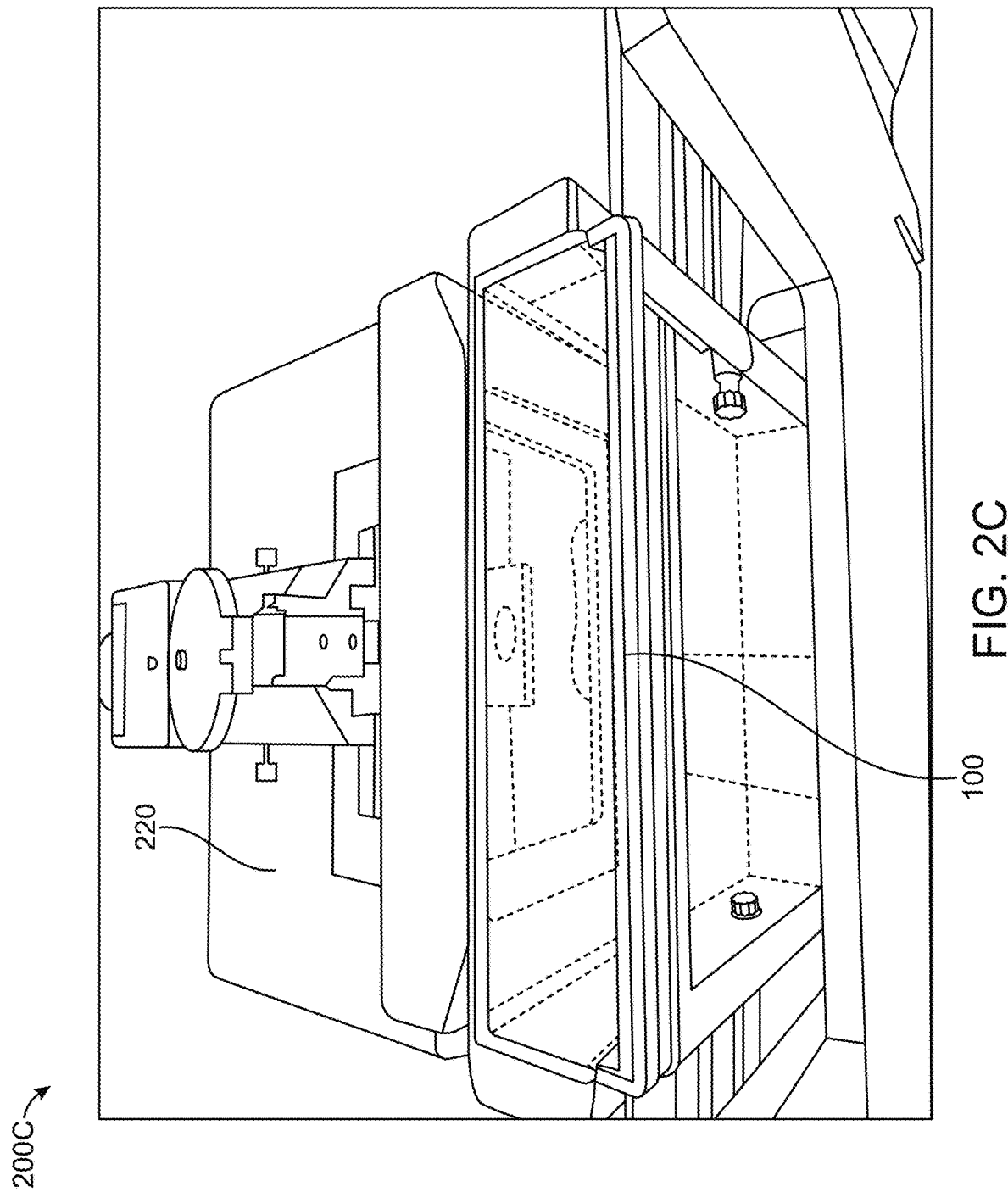

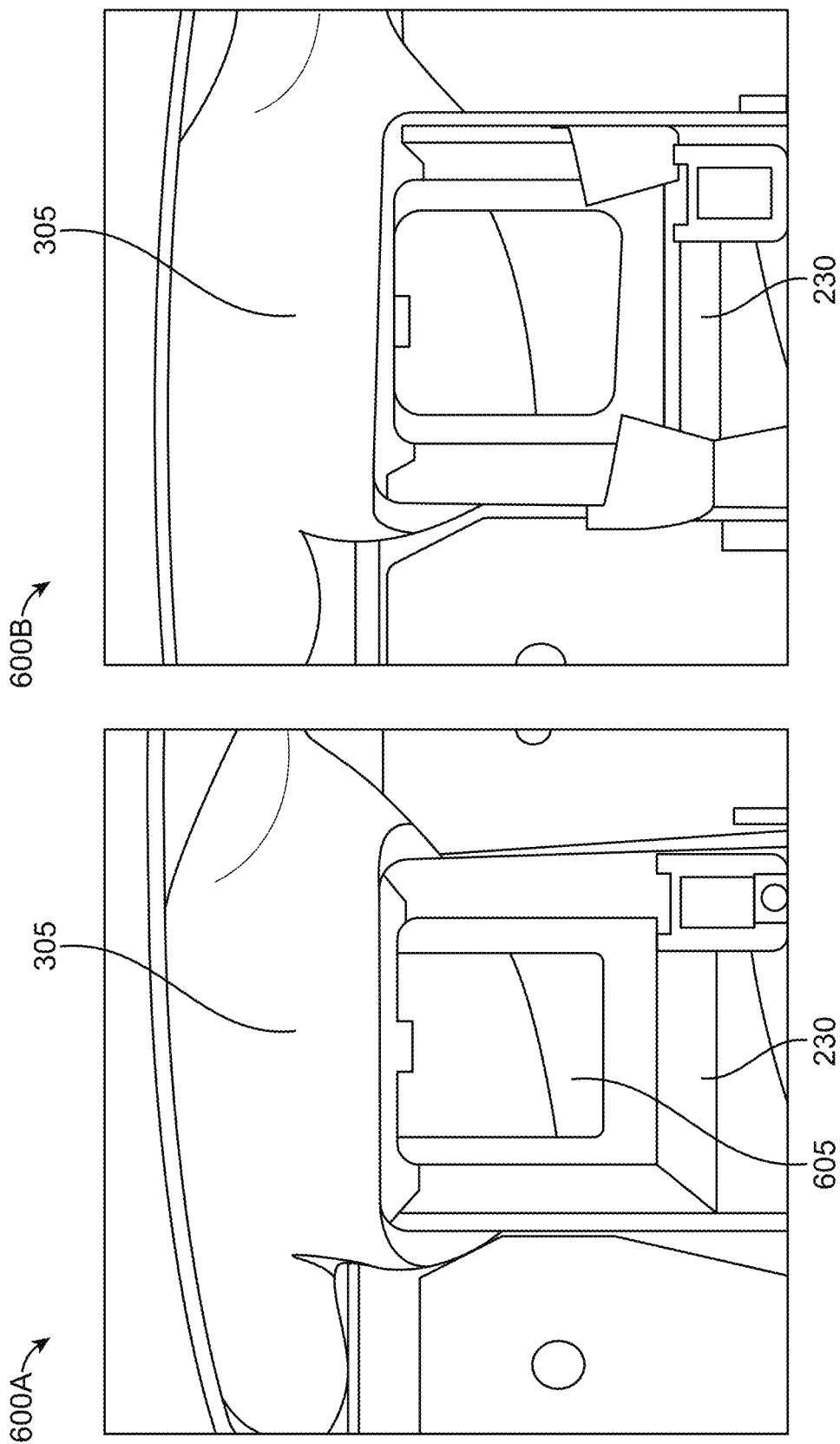

COMPRESSION PADDLES FOR BREAST BIOPSIES

CROSS-REFERENCES TO RELATED APPLICATIONS

This application is a U.S. National Stage Application under 35 U.S.C. § 371 of International Application PCT/US2019/030051, filed on Apr. 30, 2019, which claims priority under PCT Article 8 and PCT Rule 4.10 to U.S. Patent Provisional Application 62/664,682, titled "COMPRESSION PADDLES FOR BREAST BIOPSIES," filed Apr. 30, 2018, the disclosure of each of which is incorporated herein by reference in its entirety.

TECHNICAL FIELD

The present application relates generally to equipment for performing breast biopsies, including but not limited to compression paddles for breast biopsies.

BACKGROUND

Various types of biopsies may be performed on a breast to diagnose any potential issues with the breast (e.g., an anterior lesion within). Performing such a biopsy on a thin breast of a patient may be difficult. Moreover, performing a mammography on thin breasts can also be challenging.

SUMMARY

In stereotactic biopsies, a patient may lay horizontally facedown onto an upper horizontal surface of a table. The table may include an opening fully spanning from the upper horizontal surface to a lower horizontal surface. A breast of the patient (or subject) may be positioned through the opening, and may extend beneath the lower horizontal surface. With the breast extending through the opening of the table, a plate may be used to press the breast against another surface to expand a surface area of the breast while reducing the thickness. As the breast is compressed, a scanning device (e.g., X-ray machine) beneath the table may be pointed at the breast to perform a mammogram. If there are any lesions detected within the breast, a biopsy needle may be inserted at the location along the surface of the breast identified using the mammogram.

Under one technique, however, it may be difficult to perform such a biopsy when the breast is thin and thus does not extend sufficiently far through the opening. For example, the biopsy needle may puncture through a thin breast onto the opposite side of the breast and contact an imaging plate, resulting in damage to the imaging plate for the mammogram. In addition, the breast tissue may not envelop the biopsy device bowl, leading to poor suction within the breast. This may ensue with the patient undergoing excisional biopsy (sometimes referred to as a surgical biopsy) to diagnose any issues in the breast.

The technical problems of performing breast biopsies using such techniques may be solved by using two compression paddles with aligned openings pressed against the breast from opposite directions as discussed herein. The two paddles may include a reverse paddle and a compression paddle. The reverse paddle may each an aperture and the compression paddle may have one or more apertures. When pressed against the breast, the reverse paddle and the compression paddle may allow the breast to bulge out of the aperture of both paddles during the biopsy. As the breast tissue bulges out of both paddles, the breast tissue to be examined via biopsy may be enlarged, thereby avoiding or reducing the use of excisional biopsies on patients with thin breasts.

One aspect of the present disclosure is directed to a stereotactic biopsy reverse paddle. The reverse paddle may include a body. The body may be of a polygonal prismatic shape (e.g., a rectangular prism). A longitudinal surface of the body may define an aperture. The aperture may be of a polygonal shape (e.g., a rectangle). The aperture may be generally positioned toward a center of the longitudinal surface. The aperture may have a length and a width each ranging from 0.5" to 4" (inches). The aperture may at least partially engage with a portion of a breast. The longitudinal surface of the body may also include an edge portion about the aperture. The edge portion may correspond to a remainder of the longitudinal surface of the body excluding the aperture. The edge portion may at least partially engage with a portion of the breast. When the breast is pressed between the reverse paddle and a compression paddle, at least a portion may expand into the aperture of the reverse paddle and outward from a volume defined between the reverse paddle and the compression paddle.

Another aspect of the present disclosure is directed to a compression tray for stereotactic biopsy compression paddles. The compression tray may be of a polygonal prismatic shape (e.g., a rectangular prism). The compression tray may define a plurality of apertures along a longitudinal surface. Each aperture may have a diameter (or a length or width for non-circular apertures) ranging from ⅛" to 1½" (inches). The plurality of apertures may be arranged in a staggered layout along the longitudinal surface. A centroid of each aperture may be at a predefined distance from a centroid of an adjacent aperture. The compression tray may be inserted into a mounting bracket of compression paddle. The compression tray may at least partially engage with a portion of the breast. When the breast is pressed between the compression paddle and a reverse paddle, corresponding portions of a surface of the breast may expand out into the plurality of apertures.

Another aspect of the present disclosure is directed to a method of performing a mammographic breast localization through a compression paddle with apertures. The method may include placing a breast between a breast imaging platform and a compression paddle. The compression paddle may be of a polygonal prismatic shape (e.g., a rectangular prism). The compression tray may define a plurality of apertures along a longitudinal surface. Each aperture may have a diameter (or a length or width for non-circular apertures) ranging from ⅛" to 1½" (inches). The plurality of apertures may be arranged in a staggered layout on the longitudinal surface. A centroid of each aperture may be at a predefined distance from a centroid of an adjacent aperture. The method may include positioning the breast into a predefined area within the compression paddle. The method may include compressing the breast using the compression paddle and the breast imaging platform. The method may include imaging the breast, while the breast is compressing using the compression paddle and the breast imaging platform.

Another aspect of the present disclosure is directed to a system for performing breast biopsies. The system can include a mounting structure defining an opening. The system can include a first compression device. The first compression device can be received within the opening defined in the mounting structure. The first compression device can define a plurality of first apertures. The system can include a second compression device. The second compression device can define a second aperture. The second aperture can be aligned with the first compression device and be separated from the first compression device by a distance defined a breast of a subject to be biopsied to cause at least a portion of the breast to extend into the plurality of first apertures.

In some embodiments, the second compression device can be attached with a guide to set the distance between the first compression device and the second compression device. In some embodiments, the guide can include a track to align the breast with an imaging device. In some embodiments, a table can define a third aperture to position the breast of the subject over the distance defined between the first compression device and the second compression device.

In some embodiments, the second aperture of the second compression device can pass through a biopsy needle to perform the biopsy of the breast. In some embodiments, the plurality of first apertures can be arranged on the first compression device to provide a distributed compression of the breast of the subject. In some embodiments, the plurality of first apertures each can have a centroid at a predefined distance from a centroid of adjacent aperture.

In some embodiments, the first compression device can define a first central longitudinal axis aligned with a second central longitudinal axis of the second compression device. In some embodiments, the second compression device can have one or more securing elements configured to maintain the distance between the first compression device and the second compression device.

Another aspect of the present disclosure is directed to a system for performing a mammographic breast localization. The system can include a compression device. The compression device can be attached with a mounting structure. The compression device can define a plurality of apertures to provide a distributed compression of a breast of a subject. Each aperture can have a centroid at a predefined distance from a centroid of adjacent aperture. The compression device can be positioned between the imaging device and an imaging plate separated from the compression device by the breast to be imaged by the imaging device.

In some embodiments, a distance between the centroid and an edge of each aperture defined in the compression device can range between 0.125 to 1.5 inches. In some embodiments, the compression device can be received by the mounting structure to secure the compression device to the imaging device. In some embodiments, the compression device can have a polygonal prismatic shape.

Another aspect of the present disclosure is directed to a method of performing a mammographic breast localization. The method can include securing a compression device to an imaging device, the compression device defining a plurality of apertures. Each aperture can have a centroid at a predefined distance from a centroid of adjacent aperture. The method can include positioning a breast between the compression device and an imaging plate. The method can include moving the compression device and the imaging plate toward each other to provide a distributed compression of the breast of the subject along the plurality of apertures by causing least a portion of the breast to extend into the plurality of first apertures. The method can include acquiring, via the imaging device, a biomedical image of the breast positioned between the compression device and the imaging plate.

In some embodiments, the imaging device can be positioned on a first side of the compression device and the imaging plate can be positioned on a second side of the compression device, the second side opposite of the first side. In some embodiments, the imaging plate can be positioned at a posterior side of the subject and the compression device can be positioned at anterior side of the subject. In some embodiments, moving can include moving the compression device towards the imaging plate.

Another aspect of the present disclosure is directed to a method of performing biopsies. The method can include positioning a breast of a subject through a first aperture of a table on which the subject is supported. The method can include attaching a first compression device to a plate. The first compression device can define a plurality of second apertures. The method can include aligning a second compression device with the first compression device. The second compression device can define a third aperture. The method can include moving the second compression device towards the first compression device to provide a distributed compression of the breast of the subject along the plurality of second apertures by causing least a portion of the breast to extend into the plurality of second apertures.

In some embodiments, the method can include inserting a biopsy needle through the third aperture of the second compression device towards the first compression device. In some embodiments, the method can include positioning the second compression device on a track configured to move the second compression device towards the first compression device.

BRIEF DESCRIPTION OF THE FIGURES

The foregoing and other objects, aspects, features, and advantages of the disclosure will become more apparent and better understood by referring to the following description taken in conjunction with the accompanying drawings, in which:

FIGS. 2A-D depicts a reverse paddle setup on stereotactic biopsies from various perspective views;

FIGS. 6A and 6B depict a stereotactic breast biopsy of an anterior lesion;

DETAILED DESCRIPTION

Following below are more detailed descriptions of various concepts related to, and embodiments of, inventive systems, devices, apparatuses, products, and methods for breast biopsies. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes stereotactic biopsy reverse paddles.
Section B describes compression trays for stereotactic biopsy compression paddles.
Section C describes mammography through compression paddles with apertures It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Stereotactic Biopsy Reverse Paddles

Figure 1:
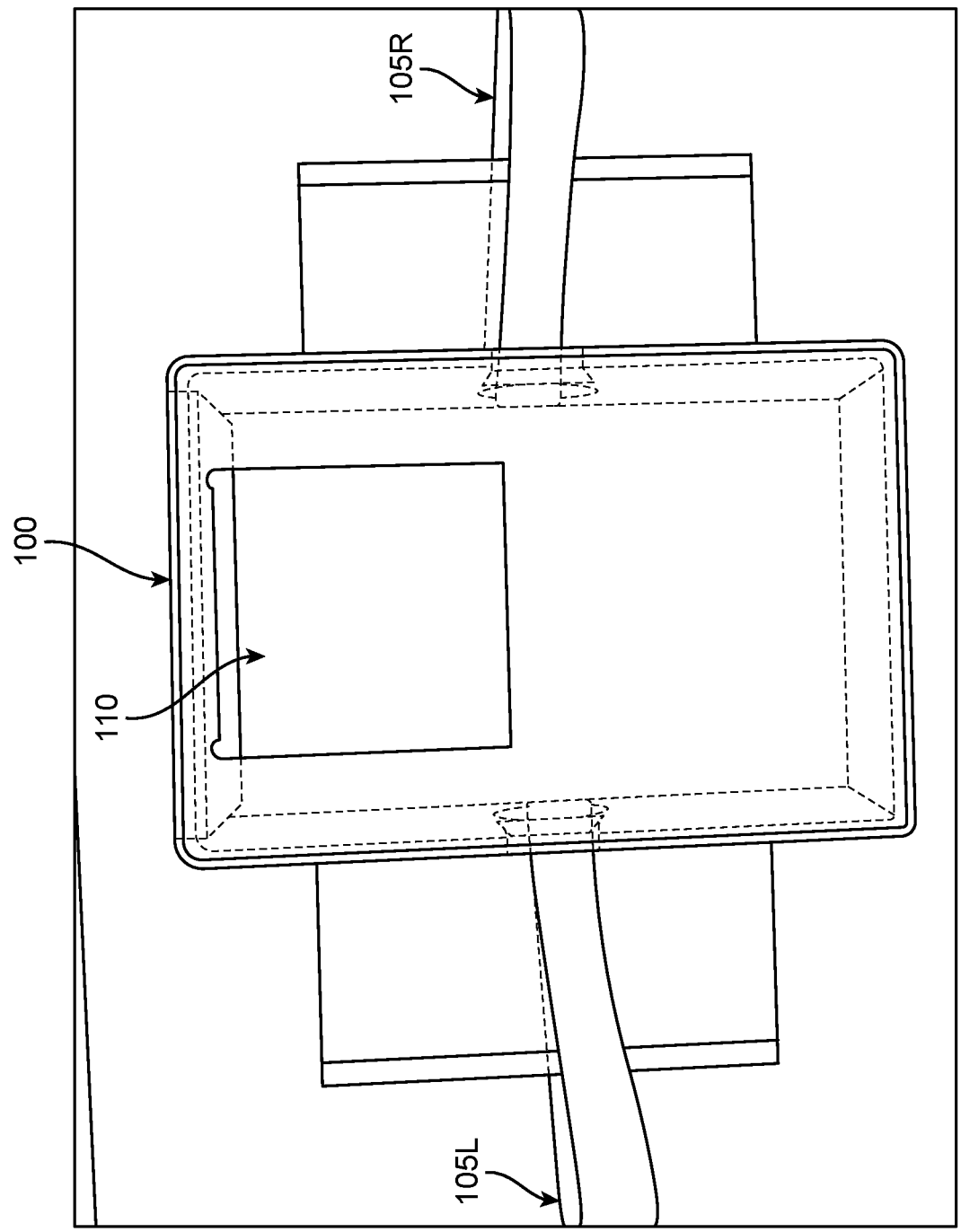
FIG. 1 depicts a reverse paddle for breast stereotactic biopsies.
Figure 2A:
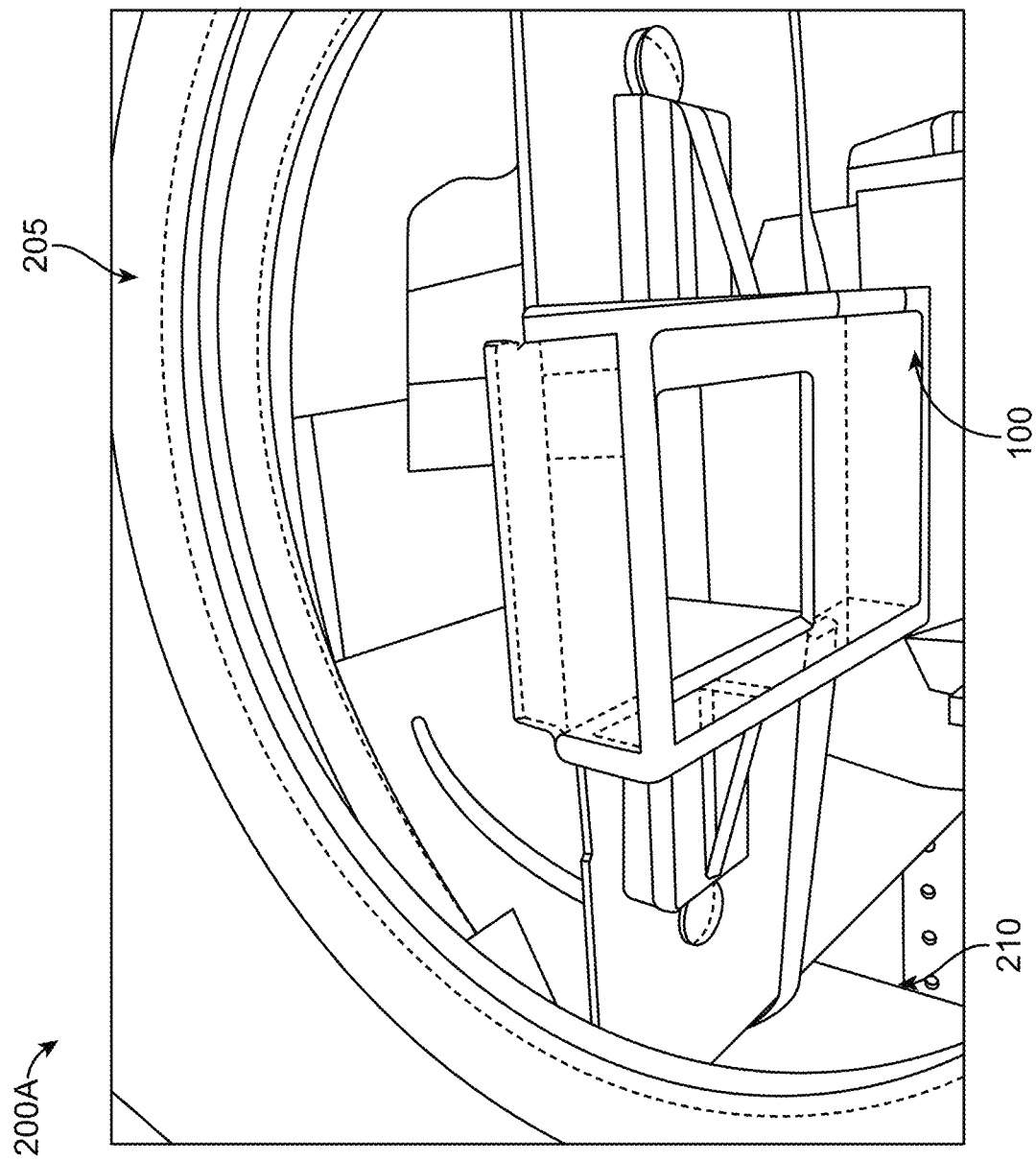
Figure 2B:
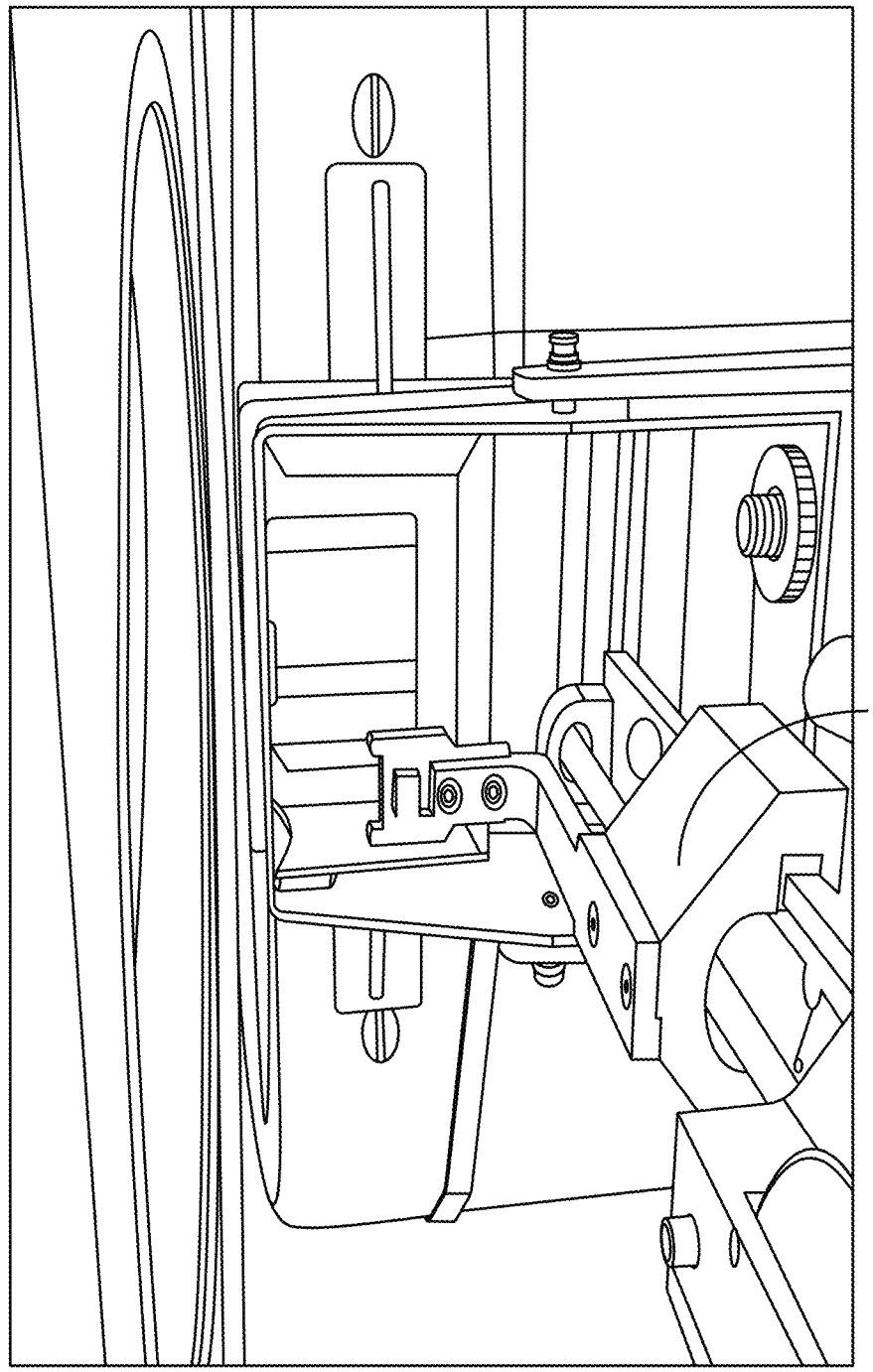
Figure 2D:
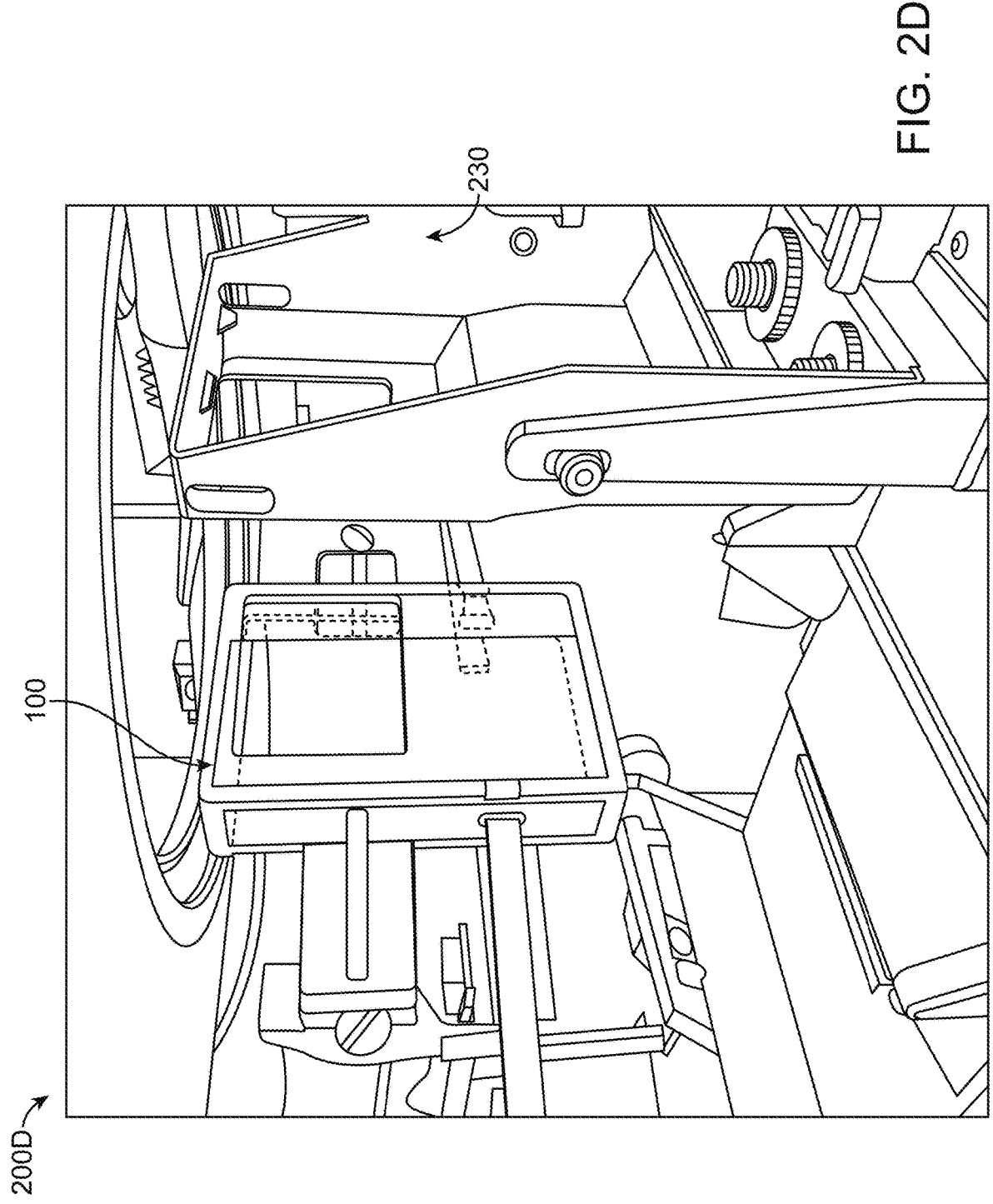

A stereotactic biopsy reverse paddle may include a body. The body may be of a polygonal prismatic shape (e.g., a rectangular prism as depicted). A longitudinal surface of the body may define an aperture. The aperture may be of a polygonal shape (e.g., a rectangle). The aperture may be generally positioned toward a center of the longitudinal surface. The aperture may have a length and a width (or a diameter for circular apertures) each ranging from 0.5" to 4" (inches). The aperture may at least partially engage with a portion of a breast. The longitudinal surface of the body may also include an edge portion about the aperture. The edge portion may correspond to a remainder of the longitudinal surface of the body excluding the aperture. The edge portion may at least partially engage with a portion of the breast. When the breast is pressed between the reverse paddle and a compression paddle, at least a portion may expand into the aperture of the reverse paddle and outward from a volume defined between the reverse paddle and the compression paddle. Referring first to FIG. 1, depicted is a reverse paddle 100 (also referred generally as a compression device). The reverse paddle 100 may include body. The body may be connected to two securing elements 105L and 105R. A body of the reverse paddle 100 may define an aperture 110. The aperture 110 may extend from one longitudinal surface of the body of the reverse paddle 100 to another longitudinal surface of the body on the opposite side.

Referring now to FIGS. 2A-D, depicted is a reverse paddle setup on stereotactic biopsies from various perspective views. First referring to a first view 200A of FIG. 2A, the reverse paddle 100 may be positioned generally below an opening 210 of a biopsy table 205. The reverse paddle 100 may have an attachment member toward the top allowing the reverse paddle 100 to hang on a plate. The reverse paddle 100 may be centered between two head screws to ensure that the aperture 110 of the reverse paddle 100 and an aperture of a compression paddle are aligned. Now referring to a second view 200B of FIG. 2B, the reverse paddle 100 may be installed on a guide 220 in line with an imaging device (e.g., an x-ray tube for mammograms). The guide 220 may be, for example, a track to direct the reverse paddle 100 to the imaging device. The imaging device can be arranged adjacent to a side of the reverse paddle 100 opposite to a side on which the breast is to be positioned.

Now referring to a third view 200C of FIG. 2C, the reverse paddle 100 may be placed or attached to the guide 220. Now referring to a fourth view 200D of FIG. 2D, the reverse paddle 110 and a compression paddle 230 may be positioned generally beneath the opening 210 of the biopsy table 205. The compression paddle 230 (also referred herein as a compression device) may also define an aperture or an opening. The aperture of the compression paddle 230 may be at least partially aligned with the aperture 110 of the reverse paddle 100 to allow for imaging and biopsies of the breast to be positioned between the reverse paddle 100 and the compression paddle 230. To align, the aperture of the compression paddle 230 with the aperture 110 of the reverse paddle 100 may face each other. The aperture of the compression paddle 230 may be longitudinally aligned with the aperture 110 of the reverse paddle 100. The compression paddle 230 can define or have a central longitudinal axis spanning a length of the compression paddle 230. The reverse paddle 100 can also define or have a central longitudinal axis spanning a length of the reverse paddle 100. To align the reverse paddle 100 and the compression paddle 230, the central longitudinal axis of the compression paddle 230 may be substantially parallel (e.g., within 15%) with the central longitudinal axis of the reverse paddle 100. With the alignment, the imaging device can be positioned on a side of the reverse paddle 100 opposite of the breast and the compression paddle 230.

Figure 3A:
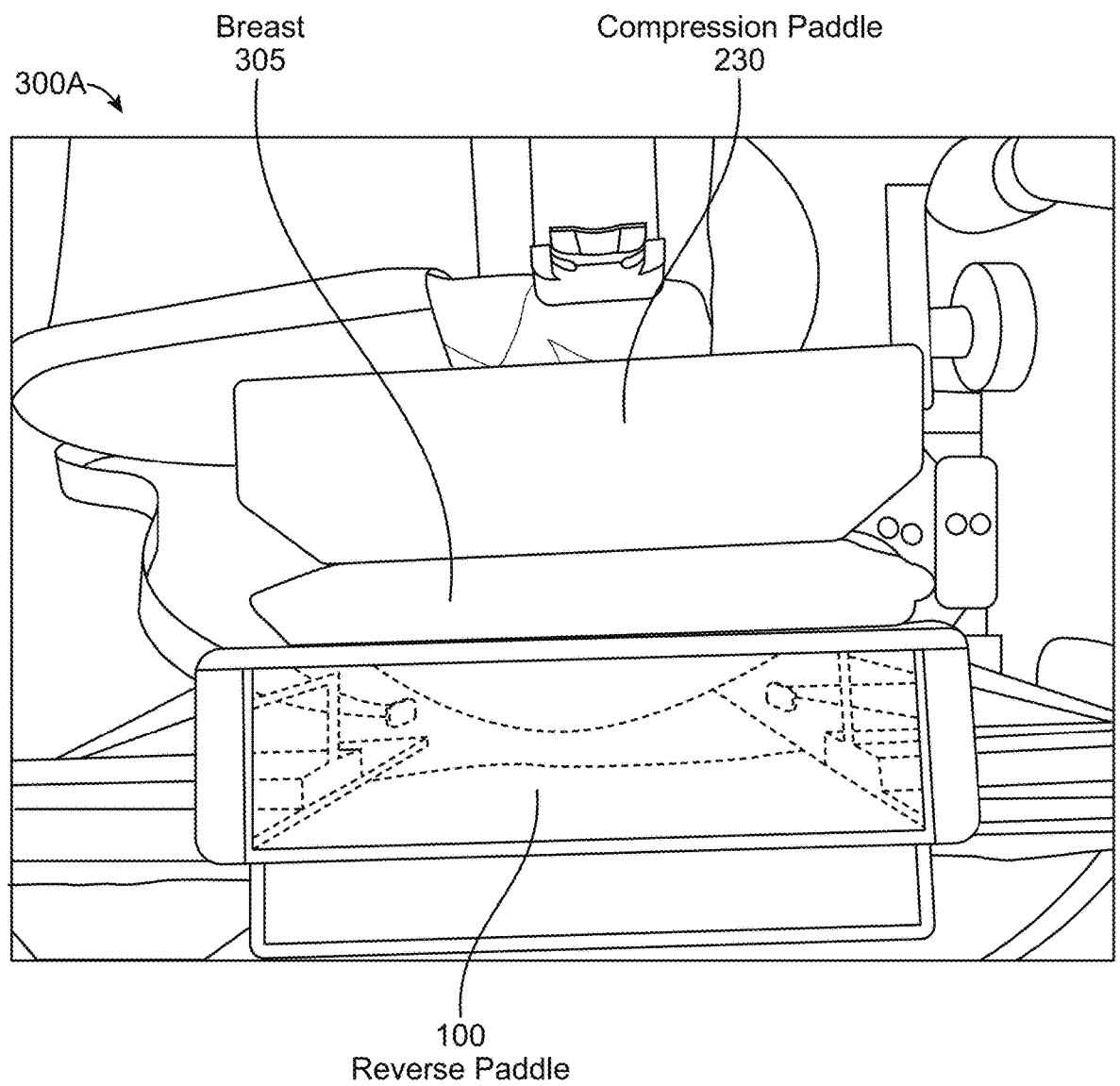
FIGS. 3A-C depicts a breast phantom secured between reverse paddle and a compression paddle.
Figure 3B:
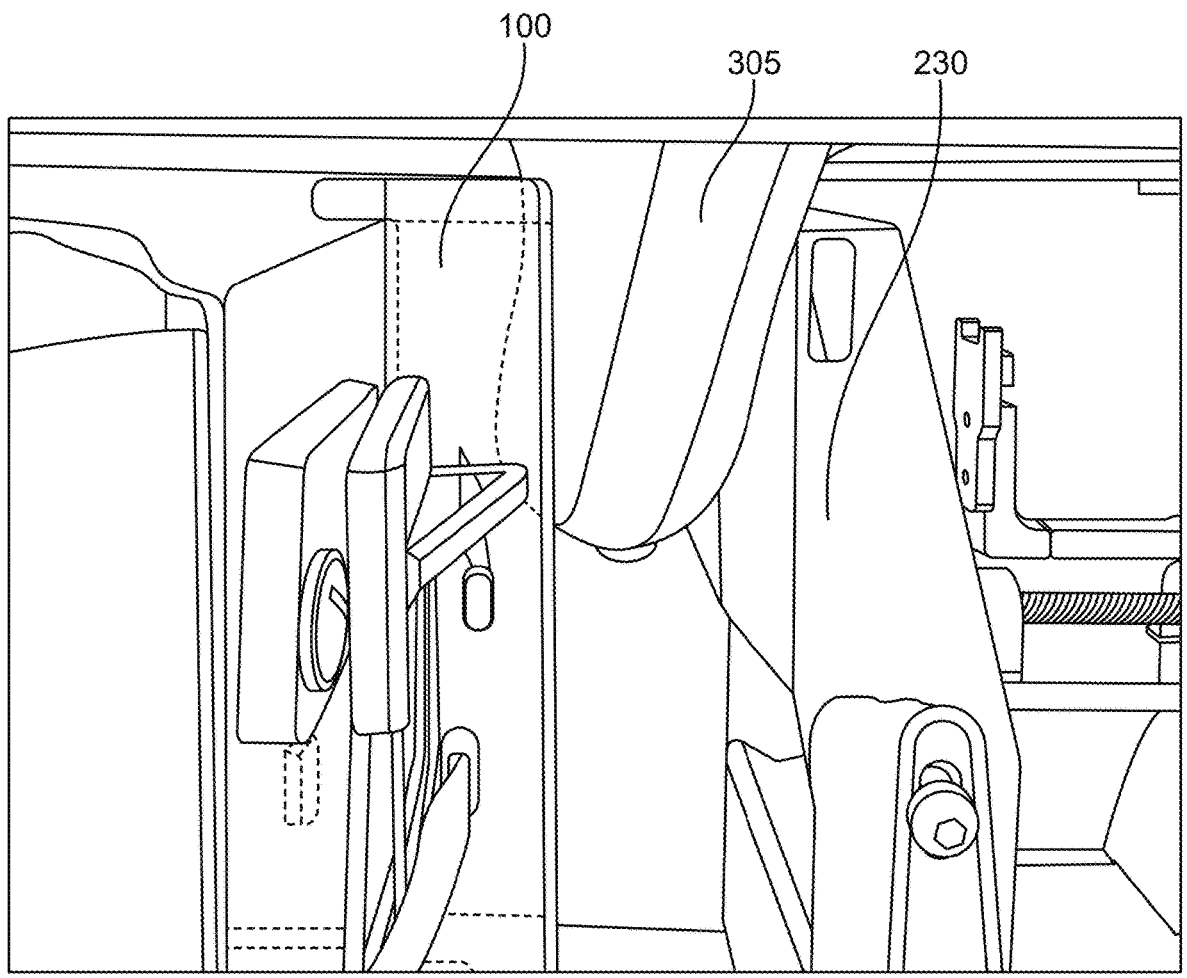
Figure 3C:
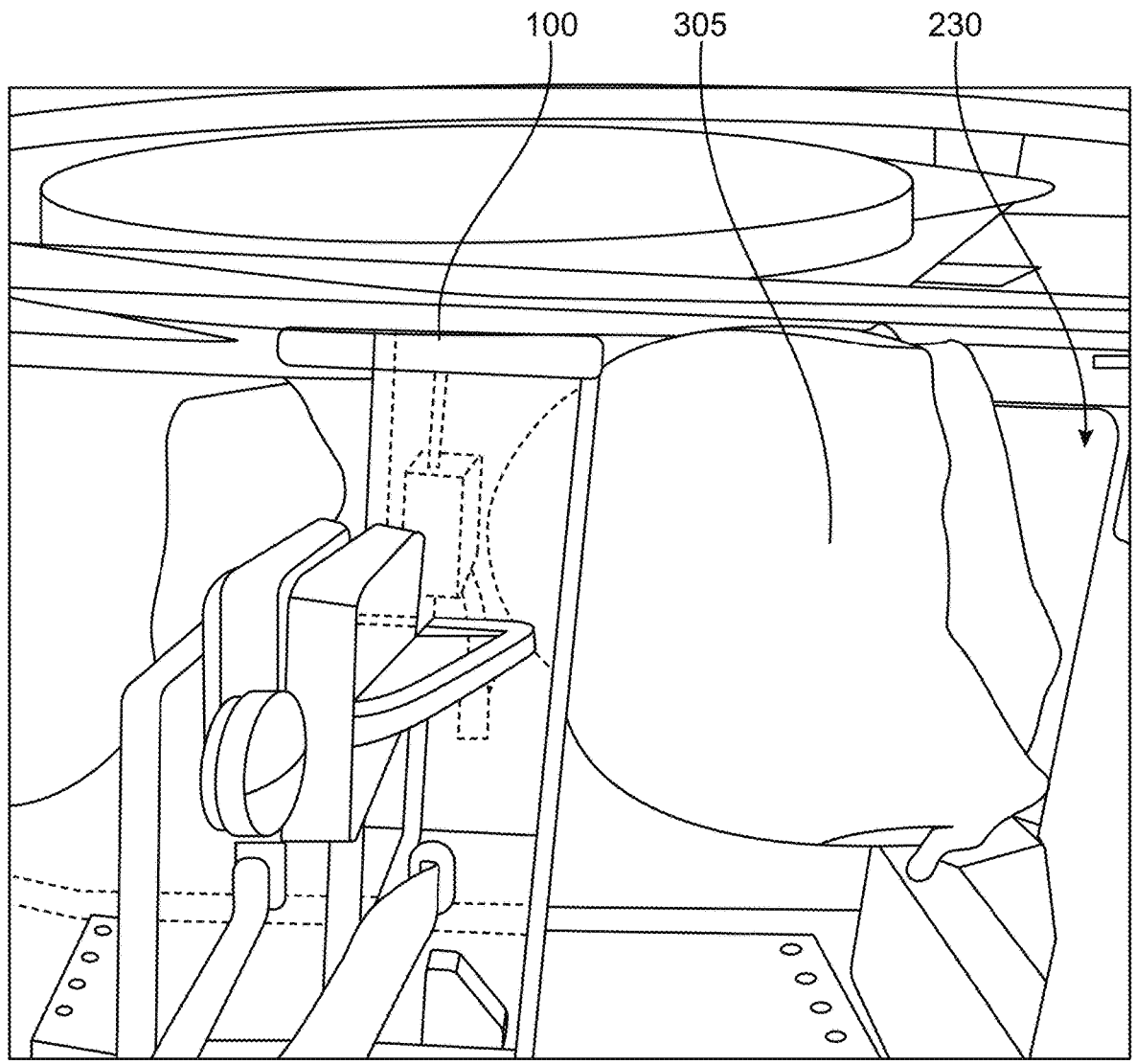

Referring now to FIGS. 3A-C, depicted is a breast phantom 305 secured between the reverse paddle 110 and the compression paddle 230. In lieu of the breast phantom 305, a breast of a subject (e.g., a human patient) can be placed and secured between the reverse paddle 110 and the compression paddle 230. Referring more specifically to FIG. 3A, the reverse paddle 110 and the compression paddle 230 may compress against the breast phantom 305. Once compressed, the breast phantom 305 may expand into the aperture 110 of the reverse paddle 100. For example, at least a portion of the breast phantom 305 on a side in contact with the reverse paddle 100 can expand into the aperture 110 of the reverse paddle 100. In addition, the breast phantom 305 when pressed may expand beyond a distance, a space, a volume defined between the compression paddle 230 and the reverse paddle 100. The distance, space, or volume can encompass or hold at least a portion of the breast of the subject. The securing elements 105L and 105R of the reverse paddle 100 can be attached or secured to the compression paddle 230 to maintain the distance, space, or volume between the compression paddle 230 and the reverse paddle 100. Referring to FIGS. 3B and 3C, the breast phantom 305 may extend through the opening 210 of the biopsy table 205, and may be compressed by the reverse paddle 100 and the compression paddle 230. As depicted, a portion of the breast phantom 305 may expand or bulge into the aperture 110 of the reverse paddle 100. In this manner, the breast tissue bulging out of the reverse paddle 100 may result in increased thickness of the breast, allowing the patient to have a biopsy.

Figures 4A, 4B:
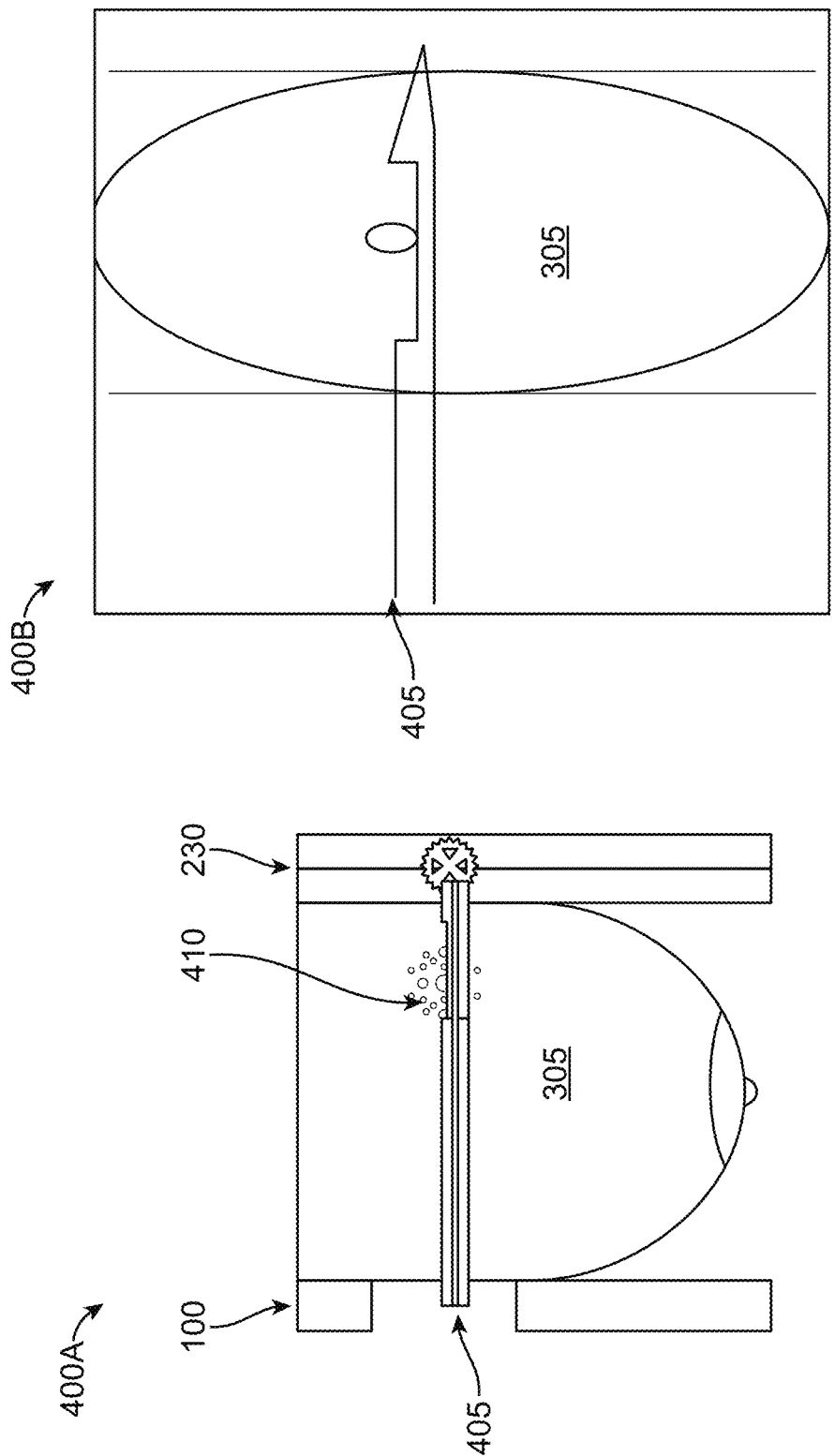
FIGS. 4A and 4B depicts a biopsy of a breast secured between reverse paddle and a compression paddle.

Referring now to FIGS. 4A and 4B, depicted are two views 400A and 400B of a biopsy of the breast 305 secured between the reverse paddle 100 and the compression paddle 230. A patient may be recommended to have a stereotactic biopsy when there is a suspicious finding on the mammogram such as calcifications or a mass. After the subject arrives, the radiologist may explain the procedure to the patient to obtain consent. The technician may place the subject prone (e.g., on stomach) on the stereotactic table. The breast 305 to be biopsied may be placed in the opening 210 in the table 205. The breast 305 may be positioned with the area of concern visualized in the window of the compression paddle 230 and compressed between the compression paddle 230 with the aperture and the reverse paddle 100 with the aperture 110. This may create more surface area to biopsy and to cover the opening of the biopsy device. Once a lesion portion 410 is identified within the breast 305, a biopsy needle 405 may be inserted through the aperture 110 of the reverse paddle 100 into the breast 305 to intersect the lesion portion 410. The biopsy needle 405 may extend through the other side of the breast 305 and into the compression paddle 230.

B. Compression Trays for Stereotactic Biopsy Compression Paddles

A compression tray for stereotactic biopsy compression paddles. The compression tray may be of a polygonal prismatic shape (e.g., a rectangular prism as depicted). The compression tray may define a plurality of apertures along a longitudinal surface. Each aperture may have a diameter (or a length or width for non-circular apertures) ranging from ⅛" to 1½" (inches). The plurality of apertures may be arranged in a random or staggered layout along the longitudinal surface of the compression tray. A centroid of each aperture may be at a predefined distance from a centroid of an adjacent aperture. The compression tray may be inserted into a mounting bracket of a compression paddle. The compression tray may at least partially engage with a portion of the breast. When the breast is pressed between the compression paddle and a reverse paddle, corresponding portions of a surface of the breast may expand out into the plurality of apertures.

Figure 5:
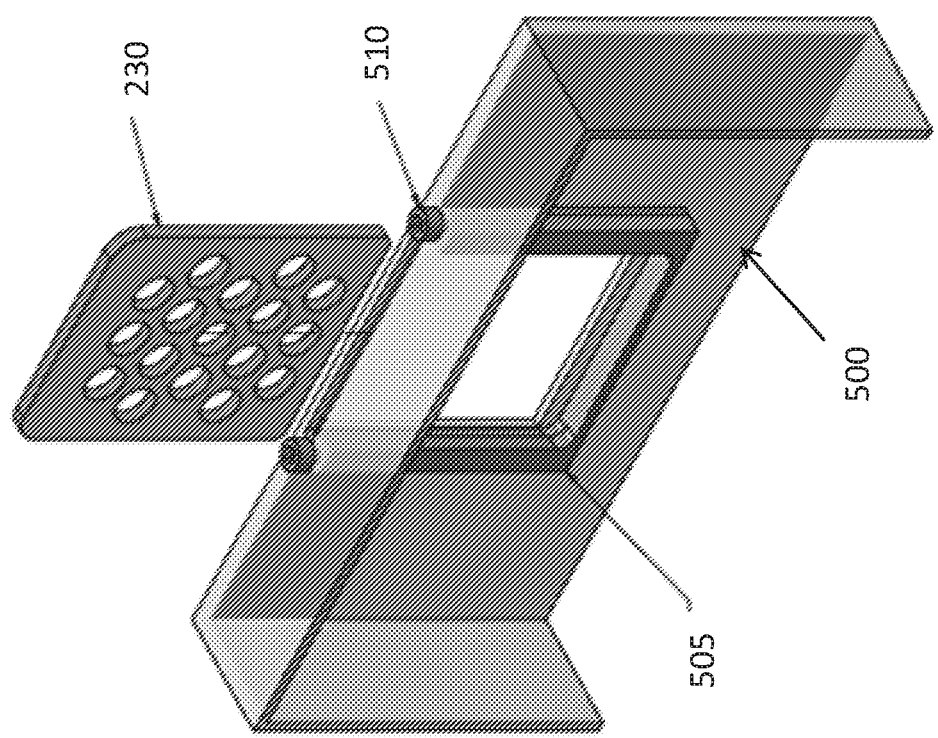
FIG. 5 depicts a compression paddle with a tray with apertures.
Figure 7A:
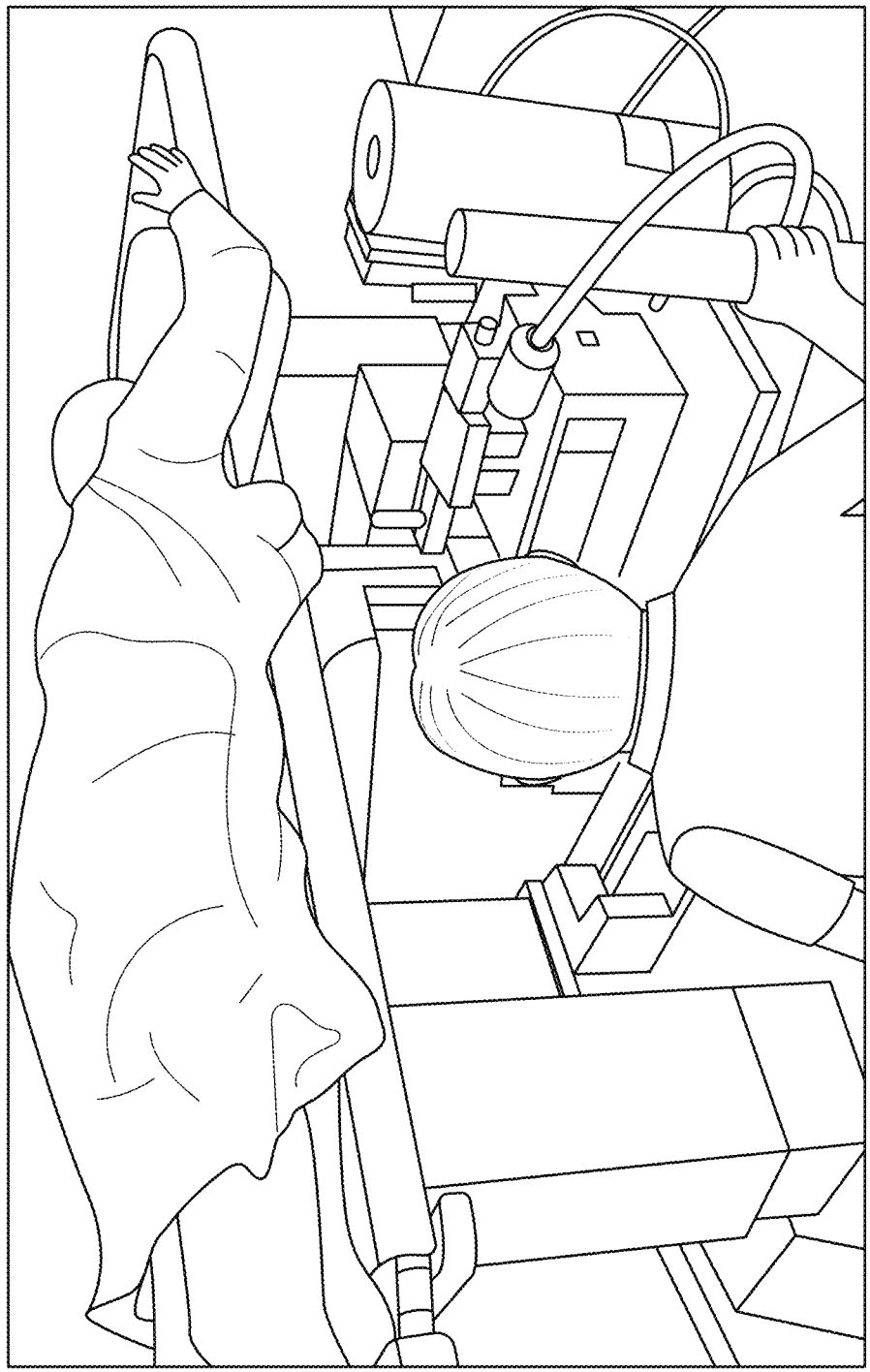
FIGS. 7A-D depict a stereotactic breast biopsy table and subject position.
Figure 7B:
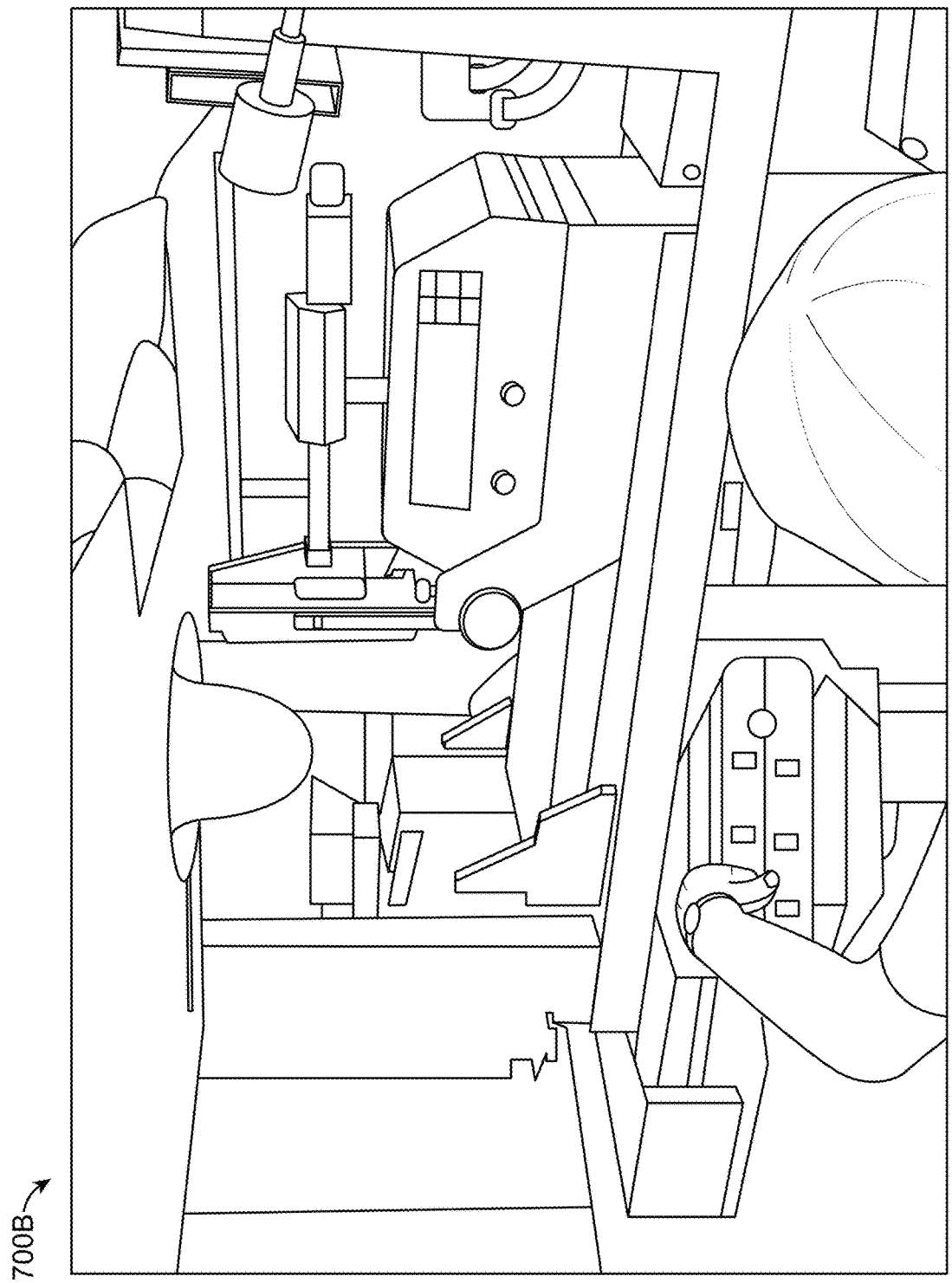
Figure 7C:
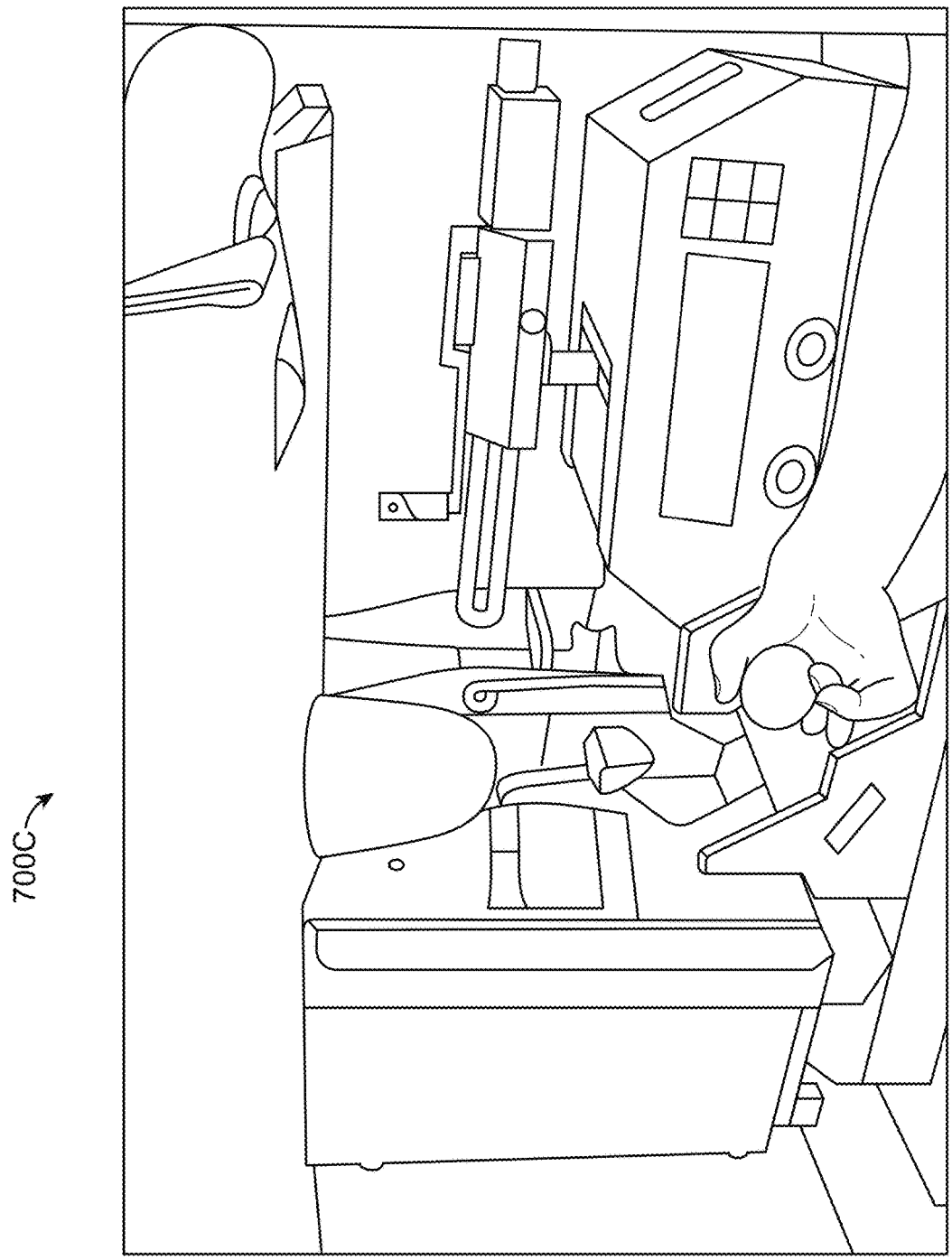
Figure 7D:
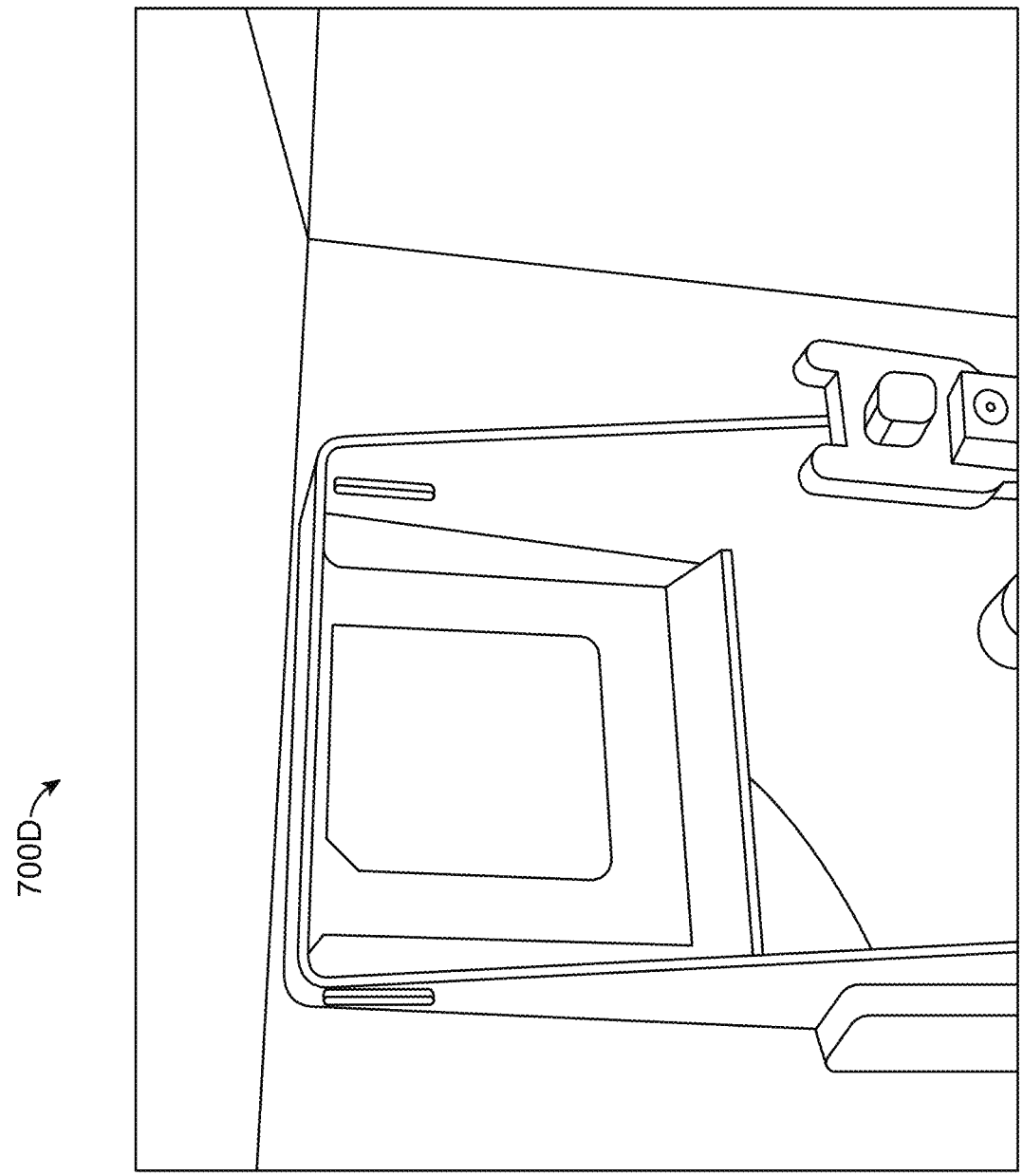

Referring now to FIG. 5, depicted is a compression paddle 230 with a compression tray 500 (sometimes referred herein as a mounting structure). The compression paddle 230 may be comprised of any material, such as a ceramic, a metallic, or an acrylic material. The compression paddle 230 may include a set of apertures. The mounting structure 500 may include a mounting bracket 505 for holding the compression tray 500. Once the compression paddle 230 is placed and secured into the mounting bracket 505, the compression paddle 230 may be held into the mounting bracket 505 using bracket mounting securing element 510 (e.g., a screw).

Referring now to FIGS. 6A and 6B, depicted are two views 600A and 600B of a stereotactic breast biopsy of an anterior lesion. A subject (e.g., a patient) may be recommended to have a stereotactic biopsy when there is a suspicious finding on the mammogram such as calcifications or a mass. After the subject arrives, the radiologist may explain the procedure to the subject to obtain consent. The technician may place the subject prone (e.g., on stomach) on the stereotactic table. The breast 305 to be biopsied may be placed in the opening 210 in the table 205. The breast 305 may be positioned with the area of concern visualized in the window of the compression paddle 230 and compressed between the compression paddle 230 with the aperture and the reverse paddle 100 with the aperture 110. By inserting the compression paddle 230 into the window of the compression tray 500, uniform compression of the breast 305 may be more achievable. In the two views 600A and 600B, without the compression paddle 230, it may be difficult to perform a stereotactic biopsy, as the breast 305 may be inadequately compressed. When the breast does not cover the aperture of the compression paddle 230, an aluminum foil 605 folded over the paddle may be used to absorb the scatter.

Referring now to FIG. 7A-D, depicted is stereotactic breast biopsy table and subject position in various perspectives. Referring specifically to view 700A of FIG. 7A, a subject may be placed on a biopsy table to lay face down. Referring specifically to view 700B of FIG. 7B, a breast of the subject may extend through an opening of the biopsy table. Referring specifically to view 700C of FIG. 7C, the compression paddle may press against the breast of the subject to commence the stereotactic biopsy. Referring specifically to view 700D of FIG. 7D, a tissue of the breast may expand out from the opening of the compression paddle. One point of the tissue may be marked for further inspection and analysis.

Figure 8A:
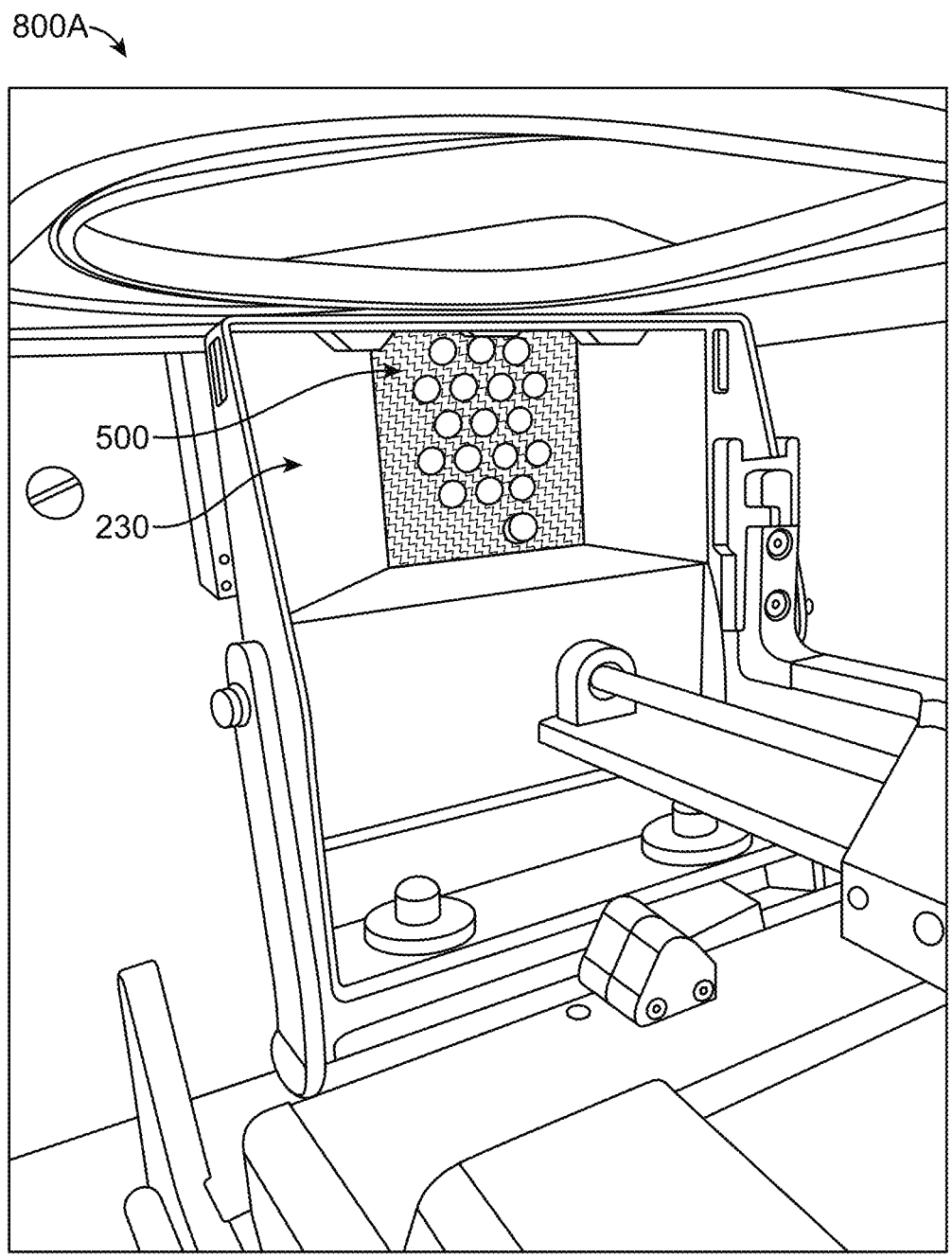
FIGS. 8A-C depict a setup for a stereotactic breast biopsy with the compression paddle installed with the tray with apertures.
Figure 8B:
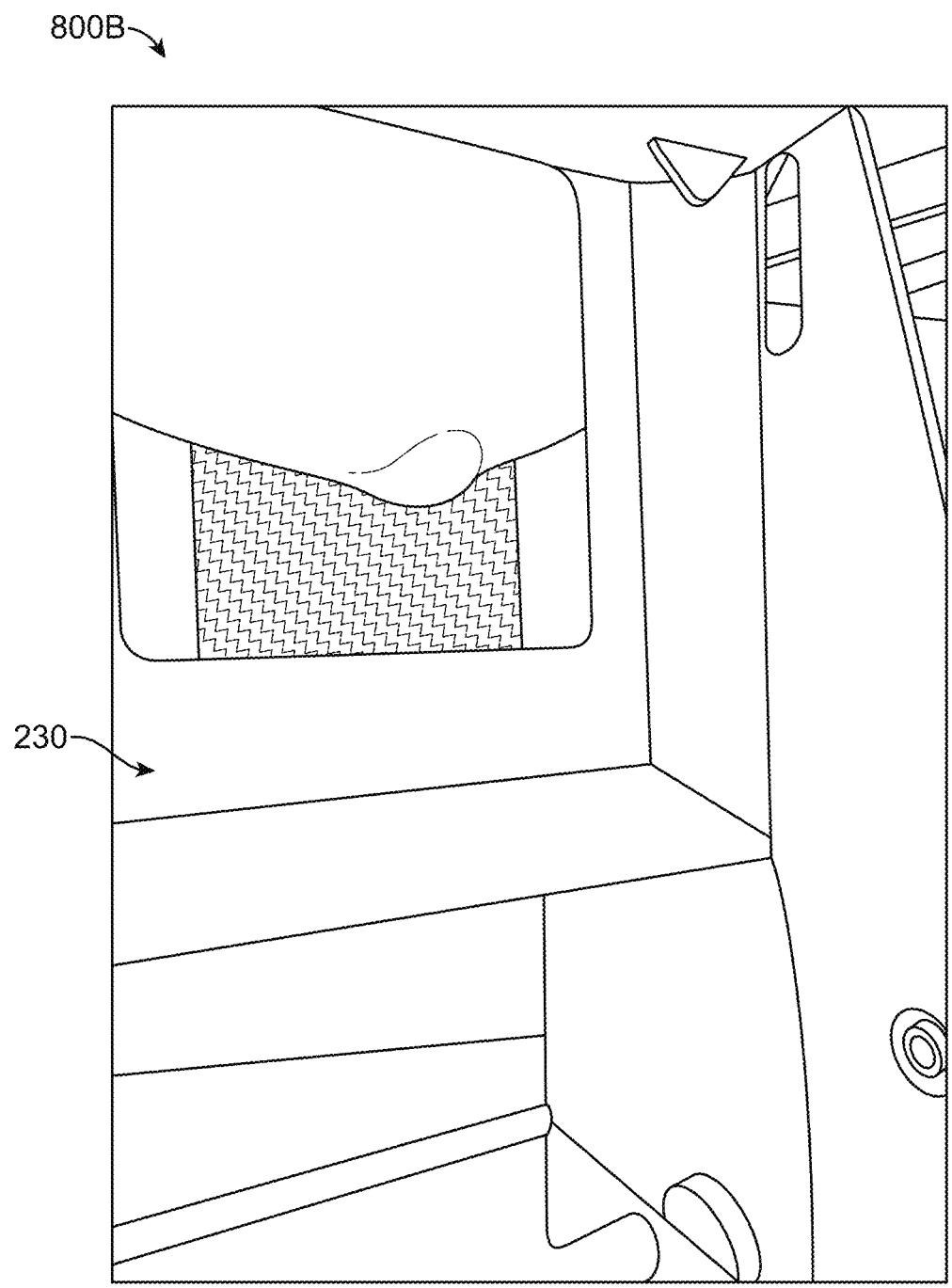
Figure 8C:
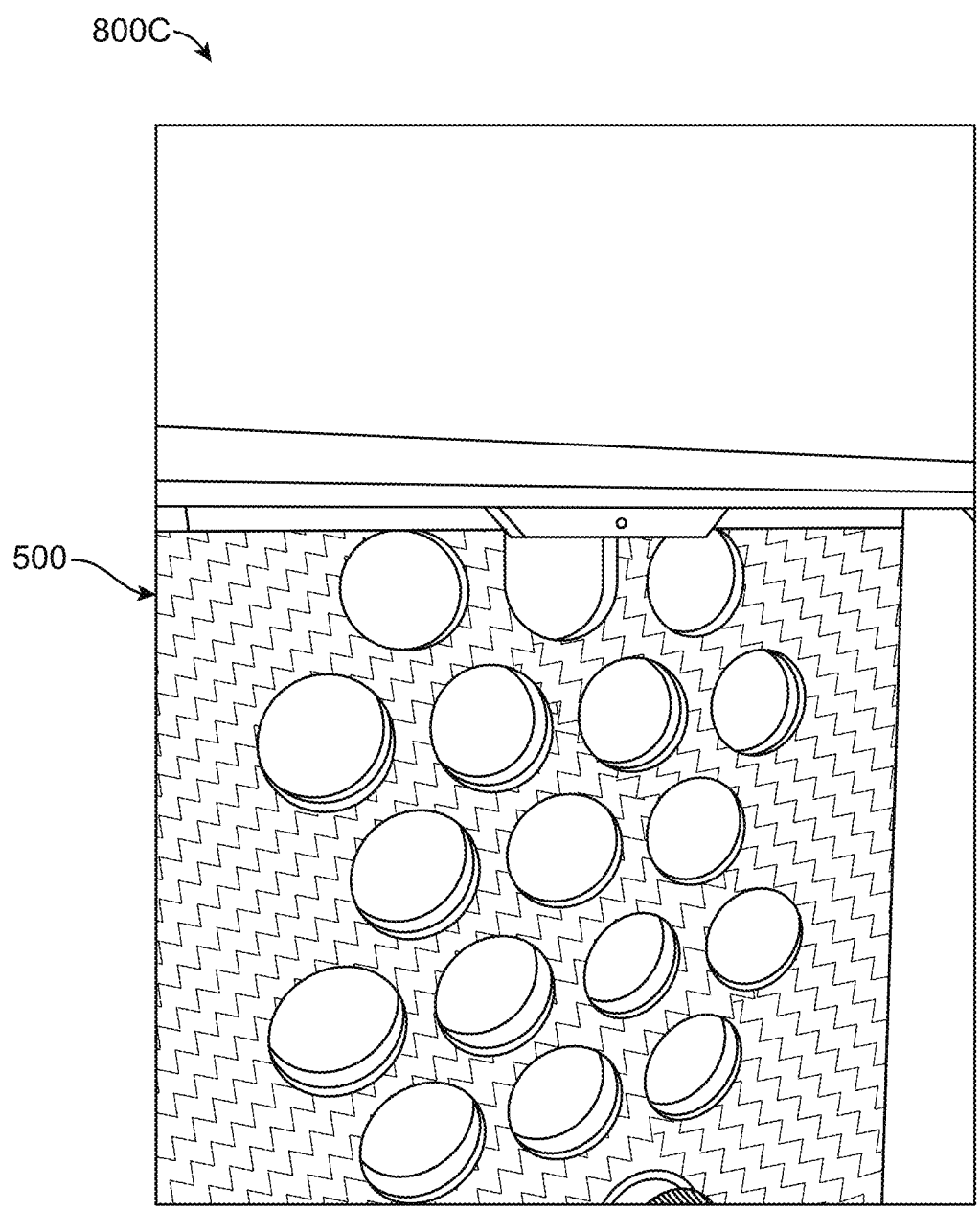

Referring now to FIG. 8A-C, depicted is a setup for a stereotactic breast biopsy with the compression paddle installed with the tray with apertures in various perspectives. Referring specifically to view 800A of FIG. 8A, the compression tray 500 may be installed with a compression paddle 230 with apertures. The compression tray 500 may be installed on a guide (e.g., the guide 220) for the stereotactic biopsy. Referring specifically to view 800B of FIG. 8B, when the compression tray 500 without the compression paddle 230 is pressed against the breast 305, adequate compression of the breast 305 may be difficult to achieve, especially in an area of the breast about the nipple. Referring specifically to view 800C of FIG. 8C, when the compression tray 500 is installed with the compression paddle 230 and is pressed against the breast 305, the breast 305 may be more compressed and the surface area of the breast 305 available for biopsy may increase.

C. Breast Localization Through Compression Paddles with Apertures

A method of performing a mammographic breast localization through a compression paddle with apertures. The method may include placing a breast between a breast imaging platform a compression paddle. The compression paddle may be of a polygonal prismatic shape (e.g., a rectangular prism). The compression tray may define a plurality of apertures along a longitudinal surface. Each aperture may have a diameter (or a length or width for non-circular apertures) ranging from ⅛" to 1½" (inches). The plurality of apertures may be arranged in a staggered layout on the longitudinal surface. A centroid of each aperture may be at a predefined distance from a centroid of an adjacent aperture. The method may include positioning the breast into a predefined area or volume within the compression paddle. The method may include compressing the breast using the compression paddle and the breast imaging platform. The method may include performing a mammographic breast localization, while the breast is compressed using the compression paddle and the breast imaging platform.

Figure 9A:
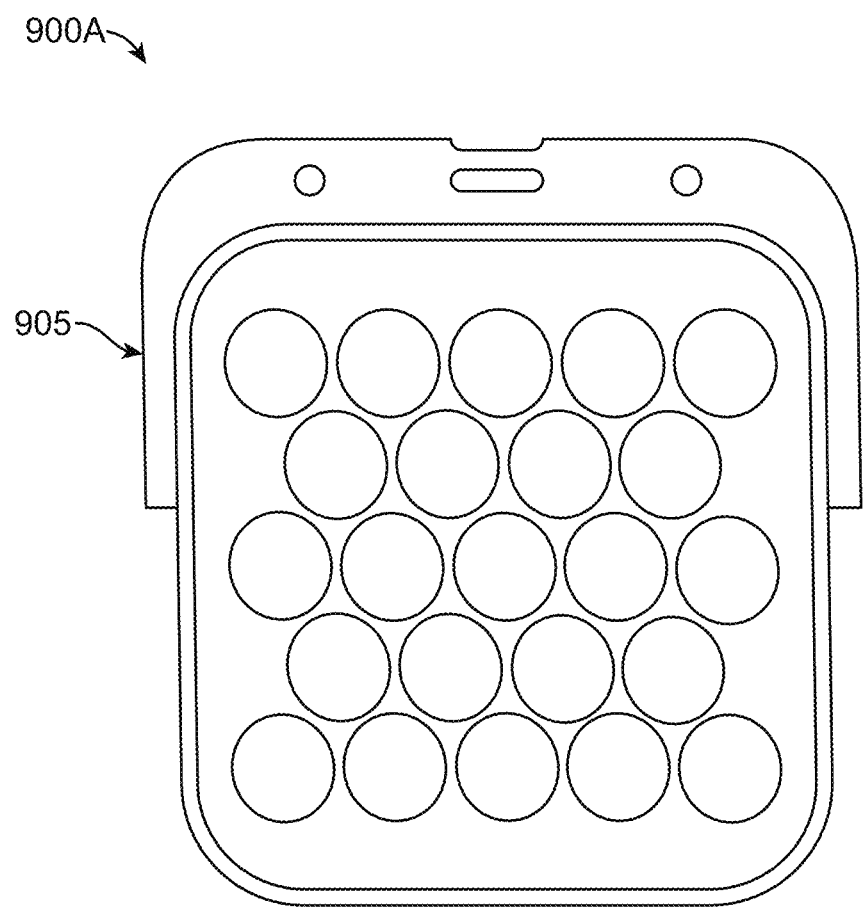
FIGS. 9A-C depict a compression paddle with apertures for a breast localization.
Figure 9B:
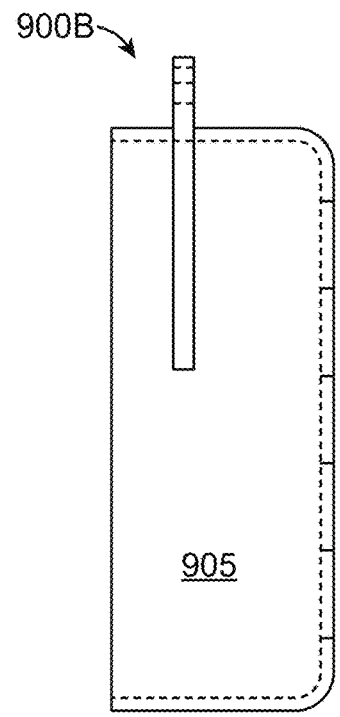
Figure 9C:
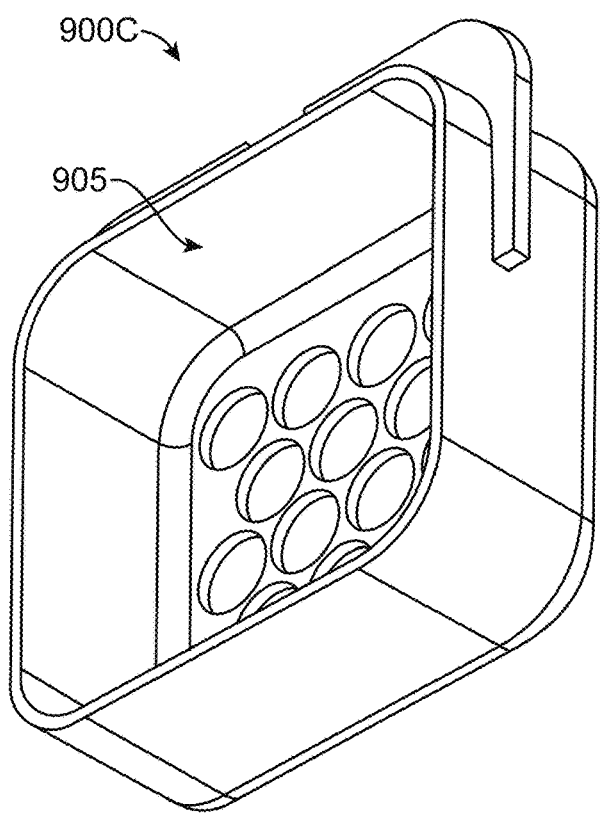

Referring now to FIGS. 9A-C, depicted is a compression paddle 905 with apertures for performing a mammographic breast localization from various perspectives shown with the dimensions of components and portions of the compression paddle 905. Referring specifically to view 900A, shown is a frontal view of the compression paddle 905. The compression paddle 905 may define a set of apertures of a predefined size. The compression paddle 905 may be of a rectangular prismatic shape. Referring specifically to view 900B, shown is a side view of the compression paddle 905. The compression paddle 905 may be of a predefined thickness. Referring specifically to view 900C, shown is an isometric view of the compression paddle 905. The compression paddle 905 may define an aperture along one longitudinal plane. The compression paddle may have a wall along the other longitudinal plane. The wall may define the set of apertures.

Figure 10A:
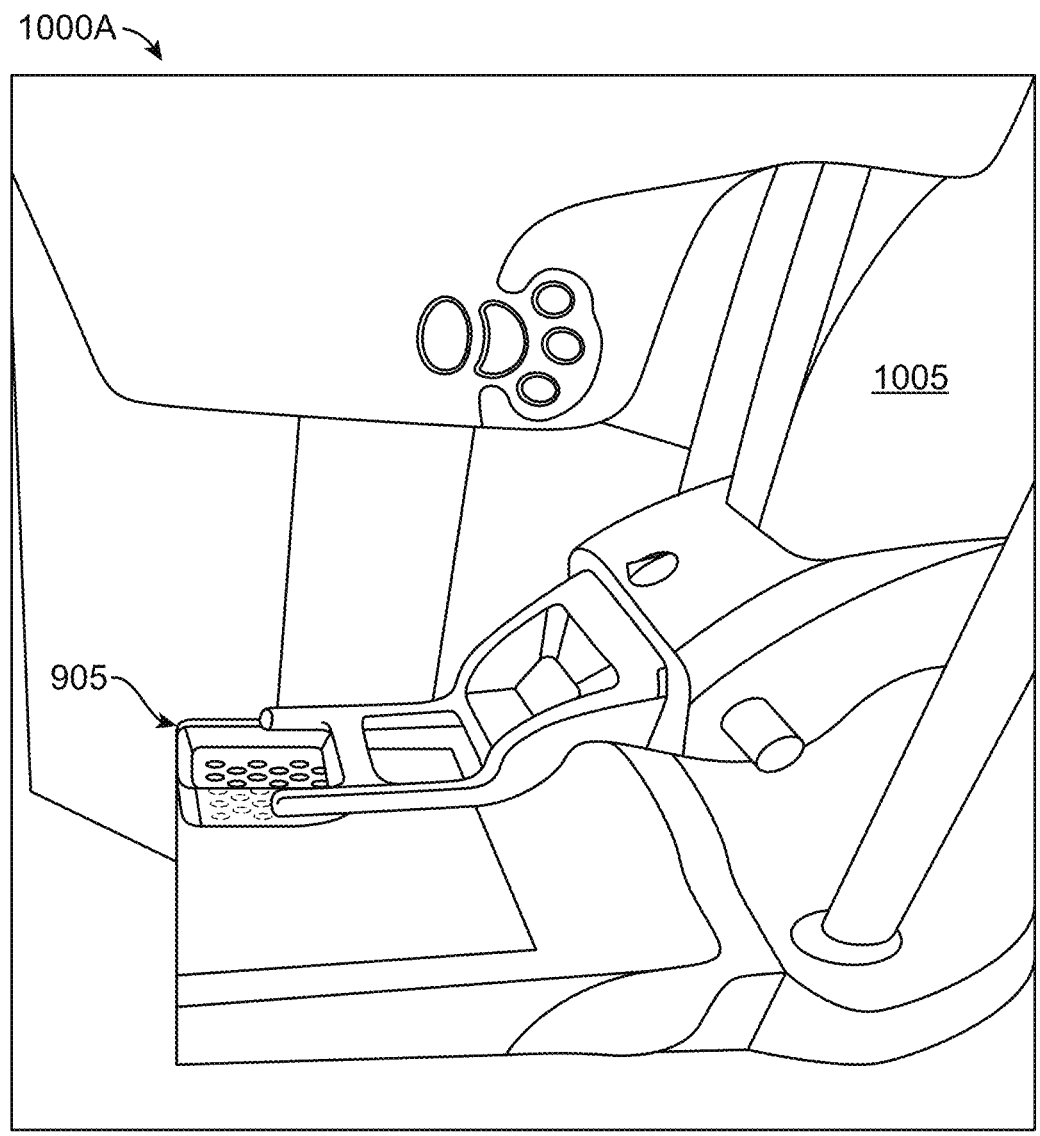
FIGS. 10A-C depict a setup with a compression paddle with apertures for a breast localization.
Figure 10B:
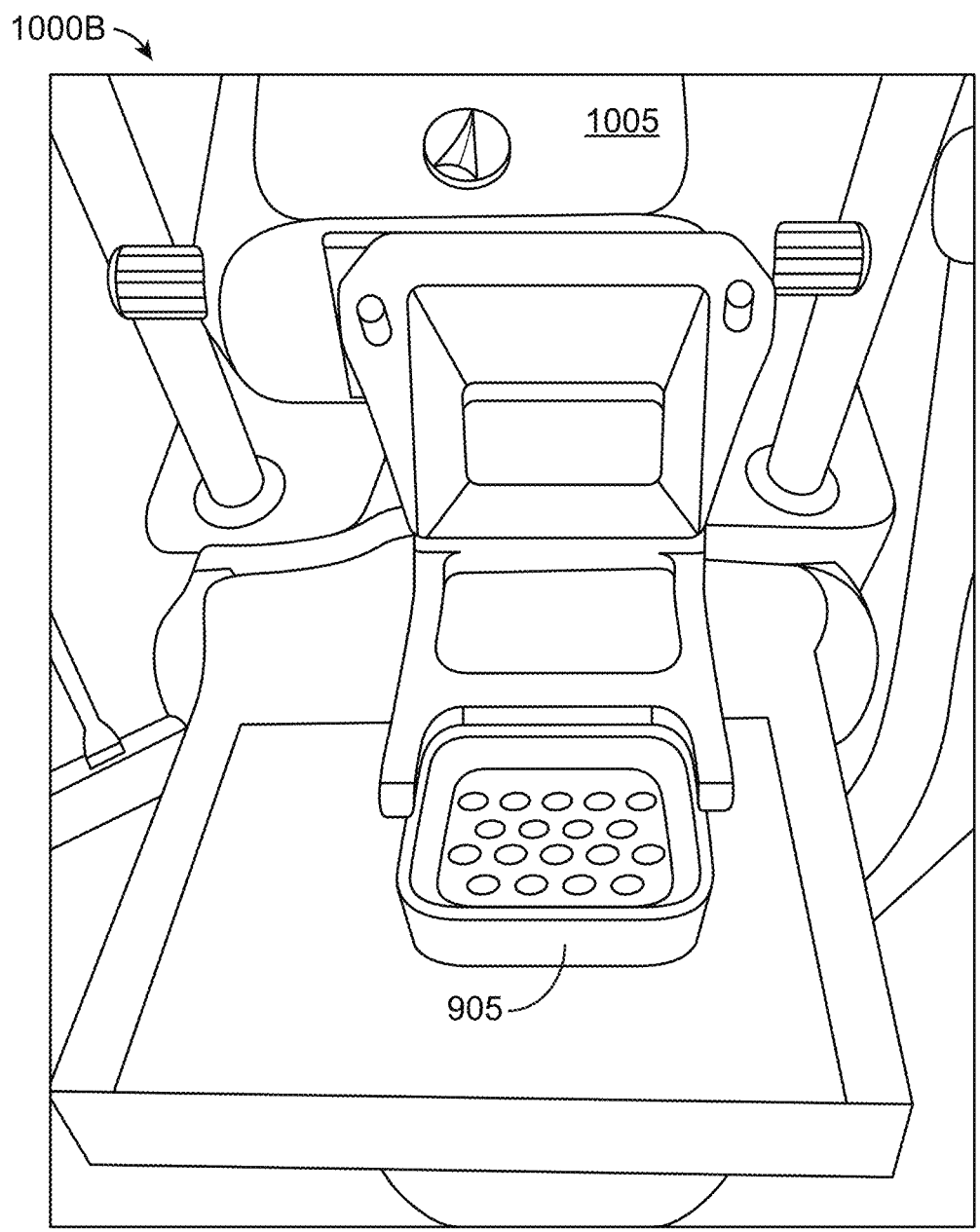
Figure 10C:
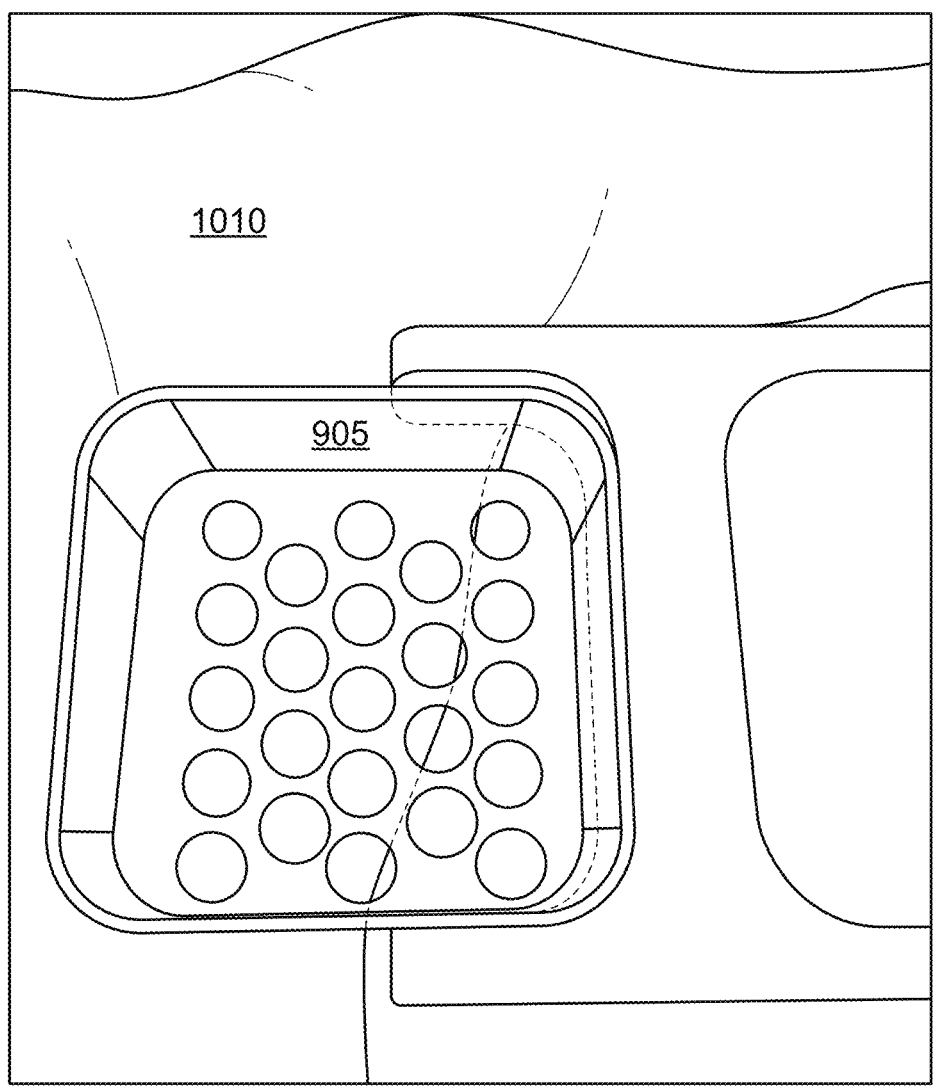

Referring now to FIGS. 10A-C, depicted is a setup with the compression paddle 905 with apertures for a breast mammography from various perspectives. A subject may be recommended to have a breast localization prior to surgery. The breast 305 may be positioned with the area of concern visualized in the window of the apertures of the compression paddle 905 and compressed by the compression paddle 905. Using the compression paddle 905 with apertures, uniform compression of the breast 305 may be more achievable. Referring specifically to view 1000A of FIG. 10A, an imaging device 1005 may include a joint or element for holding the compression paddle 905 over a plate as seen from an isometric perspective. Referring specifically to view 1000B of FIG. 10B, the compression paddle 905 may be positioned over the plate of the imaging device 1005 as seen from the frontal perspective. The imagining device 1005 can acquire a biomedical image (e.g., an X-ray) of at least a portion of the breast of the subject on the plate. Referring now to view 1000C of FIG. 10C, the compression paddle 905 may be positioned on an anterior side of a subject 1010 to against a breast of the subject 1010. The imaging plate of the imaging device 1005 can be positioned on a posterior side of the subject 1010. After securing the breast between the imaging plate and the compression paddle 905, the biomedical image of the breast can be acquired using the imaging device 1005.

Figure 11A:
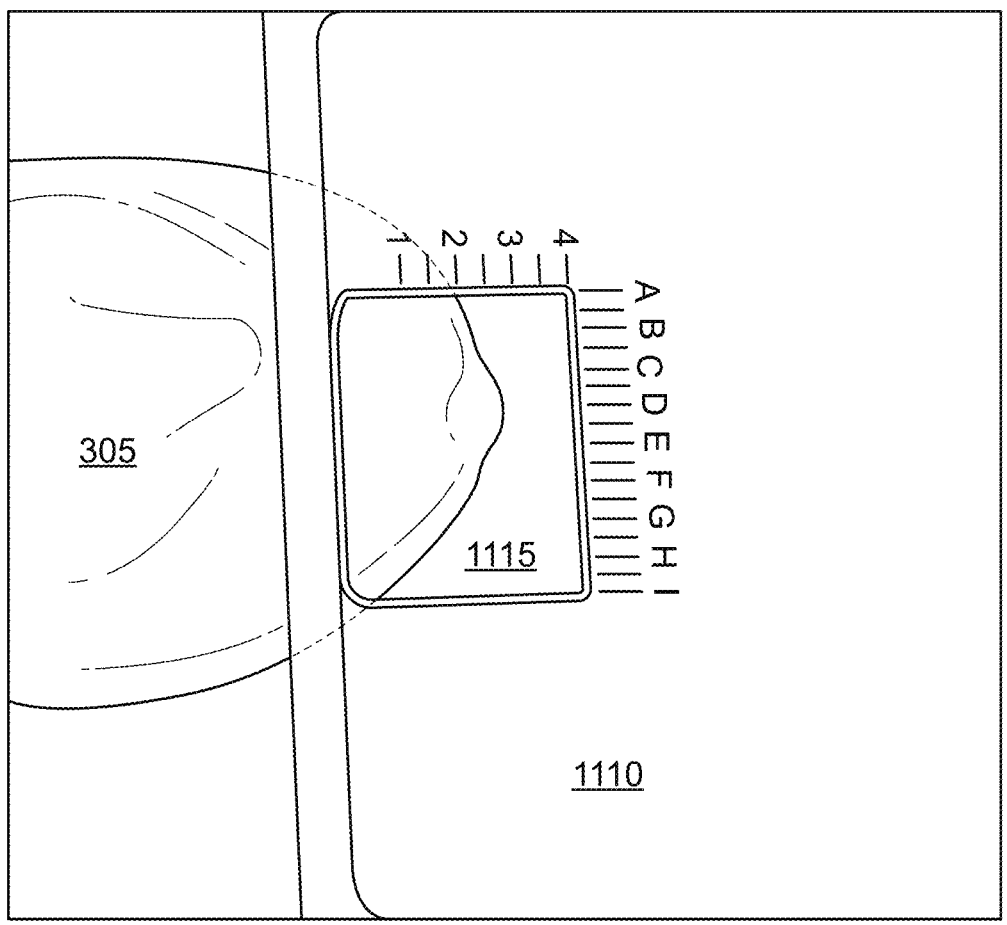
FIGS. 11A and 11B depict a breast phantom in context of a localization.
Figure 11B:
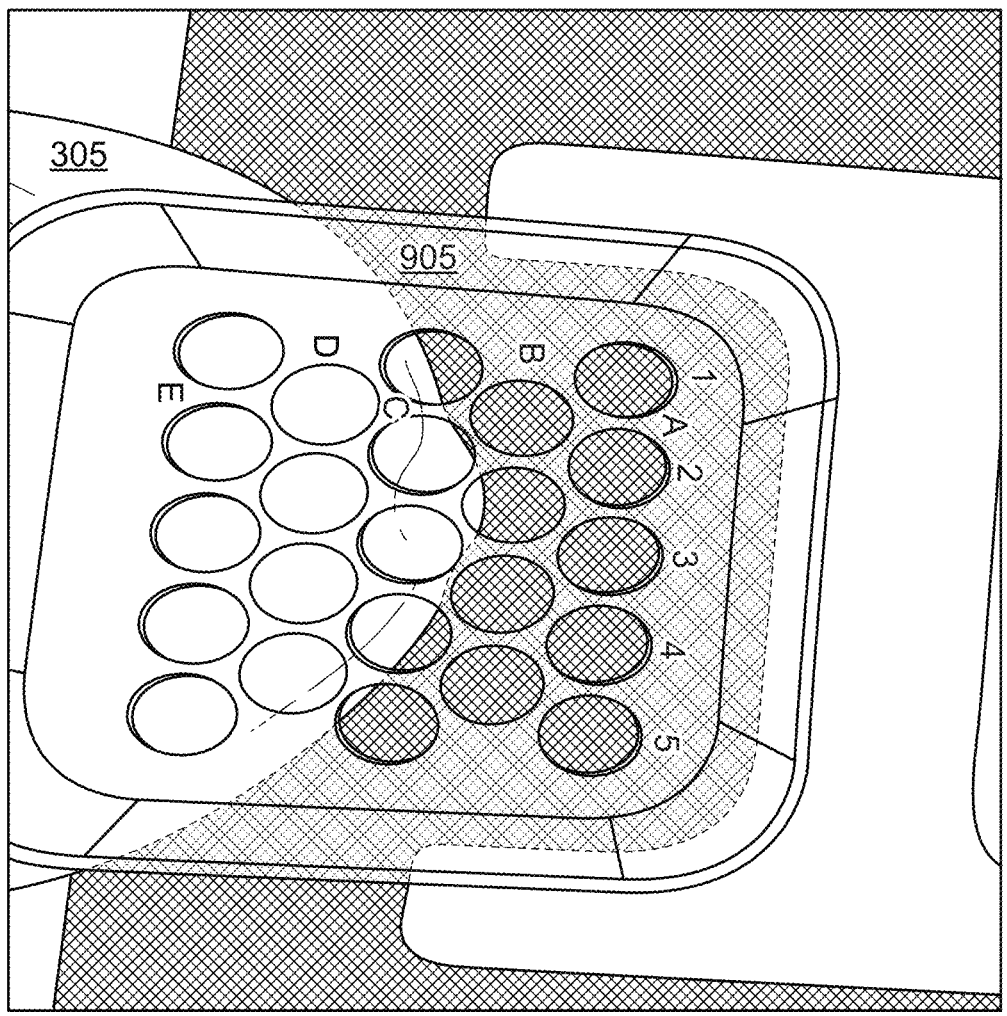

Referring now to FIGS. 11A and 11B, depicted is the breast phantom 305 in the context of a mammography. Referring to FIG. 11A, depicted is a plate 1110 with an aperture 1115 for performing breast localization of the breast phantom 305. As the aperture 1115 is sized greater than an anterior portion of the breast phantom 305, the plate 1110 may not provide adequate compression, thereby resulting in poor quality mammograms. Referring now to FIG. 11B, depicted is the compression paddle 905 with apertures pressed against the breast phantom 305. Juxtaposed with the plate 1110, the compression paddle 905 may provide a more distributed compression of the breast phantom 305, thereby yielding a greater surface area for a higher quality mammogram.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A system for performing breast biopsies, comprising:
   a first mounting structure defining an opening;
   a second mounting structure;
   a first compression device configured to be received within the opening defined in the first mounting structure, the first compression device including a first surface defining a plurality of first apertures, the plurality of first apertures arranged on the first surface of the first compression device to provide distributed compression along at least a first side of a breast; and
   a second compression device configured to be received in the second mounting structure, the second compression device including a second aperture defined through a center of the second compression device, the second aperture having a dimension larger than a dimension of at least one of the plurality of first apertures, the second compression device having a second surface about the second aperture configured to engage with at least a second side of the breast opposite of the first side, the second compression device configured to receive a biopsy needle via the second aperture to insert into the second side of the breast;
   a track positioned beneath an opening of a table and extending between the first mounting structure and the second mounting structure, wherein the second mounting structure is configured to slide along the track to vary a distance between the first compression device and the second compression device, wherein the first compression device and the second compression device are configured to:
     provide the distributed compression along at least the first side of the breast to expand at least the first side of the breast along the first surface defining the plurality of first apertures, and
     cause at least the second side of the breast to extend into the second aperture to facilitate passage of the biopsy needle from the second side of the breast along the second compression device through the first side of the breast and into the first compression device.

2. The system of claim 1, wherein the track is configured to align the second aperture of the second compression device with an imaging device.

3. The system of claim 1, wherein the plurality of first apertures is configured to provide the distributed compression of the breast to increase thickness of the second side of the breast for reception of the biopsy needle.

4. The system of claim 1, wherein the plurality of first apertures arranged in accordance with a layout to provide the distributed compression.

5. The system of claim 1, wherein the first compression device is configured to define a first central longitudinal axis substantially aligned with a second central longitudinal axis of the second compression device.

6. The system of claim 1, wherein the second compression device has one or more securing elements configured to be attached with the first compression device.

7. The system of claim 1, wherein the first plurality of apertures is arranged in a staggered layout across the first surface of the first compression device.

8. The system of claim 1, wherein the track is further configured to align the first compression device with an imaging device, the imaging device positioned on a first side of the first compression device opposite of a second side of the first compression device upon which at least the first side of the breast is to be engaged.

9. A method of facilitating breast imaging, comprising:
   attaching a first compression device in an opening of a first mounting structure, the first compression device including a first surface defining a plurality of first apertures, the plurality of first apertures arranged on the first surface of the first compression device to provide distributed compression upon at least a first side of a breast;
   attaching a second compression device in a second mounting structure, the second compression device including a second aperture, the second aperture having a dimension larger than a dimension of at least one of the plurality of first apertures, the second compression device having a second surface about the second aperture configured to engage with at least a second side of the breast opposite of the first side, the second compression device configured to receive a biopsy needle via the second aperture to insert into the second side of the breast;
   aligning, using a track, the second compression device with the first compression device and an imaging device, wherein the track is positioned beneath an opening of a table and extending between the first mounting structure and the second mounting structure, wherein the second mounting structure is configured to slide along the track to vary a distance between the first compression device and the second compression device;

moving the second compression device toward the first compression device on the track to provide the distributed compression along the first side of the breast to expand at least the first side of the breast along the first surface defining the plurality of first apertures and to cause at least the second side of the breast to extend into the second aperture to facilitate passage of the biopsy needle from the second side of the breast along the second compression device through the first side of the breast and into the first compression device; and acquiring, via the imaging device, from the first side of the breast, a biomedical image of the breast positioned between the first compression device and the second compression device.

10. The method of claim 9, wherein the plurality of first apertures is arranged in a staggered layout across the first surface of the first compression device.

11. The method of claim 9, wherein aligning further comprises aligning the first compression device with the imaging device, the imaging device positioned on a first side of the first compression device opposite of a second side of the first compression device upon which at least the first side of the breast is to be engaged.

12. A method of facilitating biopsies, comprising:

attaching a first compression device in an opening of a first mounting structure, the first compression device including a plurality of first apertures, the plurality of first apertures arranged on the first compression device to provide distributed compression along least a first side of a breast;

attaching a second compression device in a second mounting structure, the second compression device including a second aperture, the second aperture having a dimension larger than a dimension of at least one of the plurality of first apertures, the second compression device having a second surface about the second aperture configured to engage with at least a second side of the breast opposite of the first side, the second compression device configured to receive a biopsy needle via the second aperture;

aligning, using a track, the second compression device with the first compression device, wherein the track is positioned beneath an opening of a table and extending between the first mounting structure and the second mounting structure, wherein the second mounting structure is configured to slide along the track to vary a distance between the first compression device and the second compression device; and moving the second compression device along the track towards the first compression device to provide the distributed compression along at least the first side of the breast to expand at least the first side of the breast along a first surface defining the plurality of first apertures and to cause at least the second side of the breast into the second aperture to facilitate passage of the biopsy needle from the second side of the breast along the second compression device through the first side of the breast and into the first compression device.

13. The method of claim 12, wherein the plurality of first apertures is arranged in a staggered layout across the first surface of the first compression device.

14. The method of claim 12, wherein aligning further comprises aligning the first compression device with an imaging device, the imaging device positioned on a first side of the first compression device opposite of a second side of the first compression device upon which at least the first side of the breast is to be engaged.

* * * * *